(12) United States Patent
Sandler et al.

(10) Patent No.: US 9,296,786 B2
(45) Date of Patent: *Mar. 29, 2016

(54) SHORTENED SECRETED POLYPEPTIDES

(71) Applicant: TWO TO BIOTECH LTD., Jerusalem (IL)

(72) Inventors: Tamara Sandler, Jerusalem (IL); Orly Devary, Jerusalem (IL)

(73) Assignee: Two To Biotech Ltd., Jerusalem (IL)

( * ) Notice: Subject to any disclaimer, the term of this patent is extended or adjusted under 35 U.S.C. 154(b) by 32 days.

This patent is subject to a terminal disclaimer.

(21) Appl. No.: 14/146,237

(22) Filed: Jan. 2, 2014

(65) Prior Publication Data

US 2014/0121153 A1    May 1, 2014

Related U.S. Application Data

(63) Continuation-in-part of application No. 13/387,392, filed as application No. PCT/IL2010/000621 on Aug. 2, 2010, now Pat. No. 8,647,632.

(30) Foreign Application Priority Data

Aug. 2, 2009 (IL) .......................................... 200202

(51) Int. Cl.
    *C07K 14/435* (2006.01)
    *A61K 38/10* (2006.01)
    *C07K 7/08* (2006.01)
    *A61K 38/17* (2006.01)

(52) U.S. Cl.
    CPC . *C07K 7/08* (2013.01); *A61K 38/10* (2013.01); *A61K 38/17* (2013.01)

(58) Field of Classification Search
    None
    See application file for complete search history.

(56) References Cited

PUBLICATIONS

D'Alessio et al, Am J Physiol Endocrinol Metab;2004; vol. 286, pp. E882-E890.*
Chen eta l, nature biotechnology, 2003; vol. 21, pp. 294-301.*
Landgraf, Rudiger, diabetes/metabolism research and reviews, 2004, vol. 20, (sup; 2), pp. S9-S12.*

* cited by examiner

*Primary Examiner* — Bridget E Bunner
*Assistant Examiner* — Fozia Hamud
(74) *Attorney, Agent, or Firm* — Roach Brown McCarthy & Gruber, P.C.; Kevin D. McCarthy

(57) ABSTRACT

The present invention relates to an isolated polypeptide comprising (a) the amino acid sequence set forth in SEQ ID NO: 21; or (b) an amino acid sequence that is at least 95% identical to SEQ ID NO: 21, and to therapeutic treatments based thereon.

7 Claims, 10 Drawing Sheets

SEQUENCE LISTING

```
<160> NUMBER OF SEQ ID NOS: 23

<210> SEQ ID NO 1
<211> LENGTH: 67
<212> TYPE: PRT
<213> ORGANISM: Homo sapiens

<400> SEQUENCE: 1

Met Lys Pro Met Glu Arg Trp Trp Ser Arg Ala Leu Phe Thr Thr Cys
1               5                   10                  15

Pro Val Gly Pro Ser Gly Cys Ala Ala Gly Leu Leu Trp Pro Arg Asn
            20                  25                  30

Thr Asp Ala Arg Ser Pro Leu His Ser Gln Thr Leu Trp Val Cys Ser
```

```
                 35                  40                  45

Trp Ala Ala Leu Ala Gln Lys His Arg Cys Thr Val Thr Pro Ala Gln
    50                  55                  60

Pro Ala Pro
65

<210> SEQ ID NO 2
<211> LENGTH: 56
<212> TYPE: PRT
<213> ORGANISM: Homo sapiens

<400> SEQUENCE: 2

Met Pro Pro Phe Ser Val Gly Leu Val Val Val Asn Val Val Cys
1               5                   10                  15

Leu Met Leu Tyr Glu Ser Thr Thr Ile Leu Arg Leu Tyr Gly Ile Ile
            20                  25                  30

Leu Phe Met Arg Asp Leu Lys Leu Glu Val Glu Asp Ala Lys Ile Thr
        35                  40                  45

Ile Ala Leu Ala Leu Arg Asn Ser
    50                  55

<210> SEQ ID NO 3
<211> LENGTH: 70
<212> TYPE: PRT
<213> ORGANISM: Homo sapiens

<400> SEQUENCE: 3

Met Gly Met Ile Val Pro Pro Ser Leu Ala Ala Gly Gly Ala Ser
1               5                   10                  15

Thr Thr Pro Arg Leu His Ala Leu Arg Leu Thr Ser Leu Leu His Gln
            20                  25                  30

His Leu Asp Leu Cys Leu His Pro Ser Pro Leu Pro Thr Pro Pro Ser
        35                  40                  45

Ala Pro Cys Leu Ser Gly Leu Val Pro Pro Asp Ser Ser Leu Ser Val
    50                  55                  60

Leu Asp Thr Leu Gln Val
65                  70

<210> SEQ ID NO 4
<211> LENGTH: 98
<212> TYPE: PRT
<213> ORGANISM: Homo sapiens

<400> SEQUENCE: 4

Met Leu Val Phe Leu Lys Leu Trp Pro Gln Cys Leu Phe Phe Ala Leu
1               5                   10                  15

Thr Phe Phe Leu Arg Asn Cys Ile Tyr Phe Lys Asp Phe Leu Ser His
            20                  25                  30

Leu Phe Gly Ser Phe Ala Trp Asn Phe Leu Leu Ser Ser Arg Ser Met
        35                  40                  45

Asp Pro Thr Ser Cys Trp Thr Ala Pro Ile Trp Arg Ser His Arg Pro
    50                  55                  60

Leu Asn Ser Ala Pro Val Ser Glu Ser Pro Asn Tyr Pro Leu Phe Thr
65                  70                  75                  80

Trp Ser Leu Lys Pro Glu Thr Cys Pro Gly Leu Leu Val Ser Leu Tyr
                85                  90                  95

Pro Ala
```

<210> SEQ ID NO 5
<211> LENGTH: 204
<212> TYPE: DNA
<213> ORGANISM: Homo sapiens

<400> SEQUENCE: 5

```
atgaagccaa tggaaagatg gtggtcacga gccctcttca ccacctgtcc agtcggaccc      60
tctgggtgtg cagctgggct gctctggccc agaaacacag atgcacggtc accccctgcac    120 agccagaccc tctgggtgtg cagctgggct gctctggccc agaaacacag atgcacggtc    180 accccctgcac agccagcccc atga                                            204
```

<210> SEQ ID NO 6
<211> LENGTH: 168
<212> TYPE: DNA
<213> ORGANISM: Homo sapiens

<400> SEQUENCE: 6

```
atgcctccat ttcagtagg cttggttgtt gtagtcaatg tggtgtgttt gatgctatat       60
gagtctacta ctattctaag actgtatggc attattcttt ttatgagaga tctcaaatta    120
gaggttgagg atgcaaagat aactattgcc ttggccctga ggaattct                  168
```

<210> SEQ ID NO 7
<211> LENGTH: 213
<212> TYPE: DNA
<213> ORGANISM: Homo sapiens

<400> SEQUENCE: 7

```
atggggatga ttgttcctcc ttccttagct gctgcaggag gagcctccac aacacctagg      60
ttgcatgcat tgaggttgac aagtctgcta catcaacact tggacttatg tctccatccg    120 tctcccctt ctaccccacc atctgctcct tgcctctctg gccttgtgcc cccgactca      180 tcattgtctg tactggacac tctccaagta tag                                   213
```

<210> SEQ ID NO 8
<211> LENGTH: 297
<212> TYPE: DNA
<213> ORGANISM: Homo sapiens

<400> SEQUENCE: 8

```
atgttggtgt tcttgaagct ttggcctcag tgcctttct ttgctctcac attcttcctg       60
agaaattgca tctactttaa agatttcctt tcccacctat ttggatcttt tgcttggaac    120
tttctcctaa gctccaggtc catggatcct acttcctgct ggactgctcc catctggaga    180
tcccacaggc ccctcaactc agccctgtt tctgaatccc ctaattatcc tctatttact    240
tggtcactca agccagagac ttgccctggc ctccttgtct cgctgtaccc cgcctga        297
```

<210> SEQ ID NO 9
<211> LENGTH: 24
<212> TYPE: DNA
<213> ORGANISM: Homo sapiens

<400> SEQUENCE: 9

```
gaagccaatg gaaagatggt ggtc                                              24
```

<210> SEQ ID NO 10
<211> LENGTH: 23
<212> TYPE: DNA
<213> ORGANISM: Homo sapiens

```
<400> SEQUENCE: 10
ggtgaccgtg catctgtgtt tct                                            23

<210> SEQ ID NO 11
<211> LENGTH: 25
<212> TYPE: DNA
<213> ORGANISM: Homo sapiens

<400> SEQUENCE: 11
ggcttggttg ttgtagtcaa tgtgg                                          25

<210> SEQ ID NO 12
<211> LENGTH: 24
<212> TYPE: DNA
<213> ORGANISM: Homo sapiens

<400> SEQUENCE: 12
attcctcagg gccaaggcaa tagt                                           24

<210> SEQ ID NO 13
<211> LENGTH: 24
<212> TYPE: DNA
<213> ORGANISM: Homo sapiens

<400> SEQUENCE: 13
ttgttcctcc ttccttagct gctg                                           24

<210> SEQ ID NO 14
<211> LENGTH: 26
<212> TYPE: DNA
<213> ORGANISM: Homo sapiens

<400> SEQUENCE: 14
tccagtacag acaatgatga gtcggg                                         26

<210> SEQ ID NO 15
<211> LENGTH: 24
<212> TYPE: DNA
<213> ORGANISM: Homo sapiens

<400> SEQUENCE: 15
ttcttgaagc tttggcctca gtgc                                           24

<210> SEQ ID NO 16
<211> LENGTH: 24
<212> TYPE: DNA
<213> ORGANISM: Homo sapiens

<400> SEQUENCE: 16
gtctctggct tgagtgacca agta                                           24

<210> SEQ ID NO 17
<211> LENGTH: 14
<212> TYPE: PRT
<213> ORGANISM: Homo sapiens
```

```
<400> SEQUENCE: 17

Gln Lys His Arg Cys Thr Val Thr Pro Ala Gln Pro Ala Pro
1               5                   10

<210> SEQ ID NO 18
<211> LENGTH: 14
<212> TYPE: PRT
<213> ORGANISM: Homo sapiens

<400> SEQUENCE: 18

Glu Asp Ala Lys Ile Thr Ile Ala Leu Ala Leu Arg Asn Ser
1               5                   10

<210> SEQ ID NO 19
<211> LENGTH: 14
<212> TYPE: PRT
<213> ORGANISM: Homo sapiens

<400> SEQUENCE: 19

Pro Pro Asp Ser Ser Leu Ser Val Leu Asp Thr Leu Gln Val
1               5                   10

<210> SEQ ID NO 20
<211> LENGTH: 14
<212> TYPE: PRT
<213> ORGANISM: Homo sapiens

<400> SEQUENCE: 20

Pro Glu Thr Cys Pro Gly Leu Leu Val Ser Leu Tyr Pro Ala
1               5                   10

<210> SEQ ID NO 21
<211> LENGTH: 15
<212> TYPE: PRT
<213> ORGANISM: Homo sapiens

<400> SEQUENCE: 21

Lys Pro Glu Thr Cys Pro Gly Leu Leu Val Ser Leu Tyr Pro Ala
1               5                   10                  15

<210> SEQ ID NO 22
<211> LENGTH: 15
<212> TYPE: PRT
<213> ORGANISM: Homo sapiens

<400> SEQUENCE: 22

Ser His Leu Phe Gly Ser Phe Ala Trp Asn Phe Leu Leu Ser Ser
1               5                   10                  15

<210> SEQ ID NO 23
<211> LENGTH: 8
<212> TYPE: PRT
<213> ORGANISM: Homo sapiens

<400> SEQUENCE: 23

Leu Leu Val Ser Leu Tyr Pro Ala
1               5
```

SHORTENED SECRETED POLYPEPTIDES

CROSS-REFERENCE TO RELATED APPLICATION

This application is a continuation-in-part of application Ser. No. 13/387,392 (filed on 27 Jan. 2012; now U.S. Pat. No. 8,647,632), which is the National Stage of International Application No. PCT/IL2010/000621, filed on Aug. 2, 2010, which claims priority to Israeli Patent application serial number 200202, filed on Aug. 2, 2009.

FIELD OF THE INVENTION

The present invention relates to novel proteins, to the nucleic acids encoding the same and to compositions comprising the same, the antibodies that specifically recognize said proteins, as well as to their uses in therapeutic and diagnostic methods.

BACKGROUND OF THE INVENTION

The discussion in this section is not limited to subject matter that qualifies as "prior art" against the present invention. Therefore, no admission of such prior art status shall be implied or inferred by reason of inclusion of particular subject matter in this discussion, and no declaration against the present inventors' interests shall be implied by reason of such inclusion.

All publications mentioned throughout this application are fully incorporated herein by reference, including all references cited therein.

Tissue-specific proteins and their expression levels can be excellent indicators for the organism's health state as well as potential targets for treatment in case of disease.

Diseases which affect human beings may be categorized according to the mechanism of their cause. For example, diseases that have an immunological component or etiology include infectious diseases, acute and chronic inflammatory diseases, cancer, transplantation and autoimmune diseases.

The term inflammatory bowel disease (IBD) covers a group of disorders in which the intestines become inflamed (red and swollen), probably as a result of an immune reaction of the body against its own intestinal tissue, and therefore it is considered an auto-immune disorder.

Inflammatory diseases include sepsis, endotoxemia, pancreatitis, uveitis, hepatitis, peritonitis, keratitis, SIRS and injury-induced inflammation.

Diseases linked to fertility include male infertility and female infertility. Male infertility can be caused by a variety of problems. Some of the more common disorders are listed below:

Deficient Sperm Production: Ninety percent of male infertility is caused by the failure to produce enough sperm. Azzospermia occurs when no sperm is produced while oligospermia is diagnosed when few sperm are produced;

Varicocele;

Other Disorders: abnormal development or damage of the testes (caused by endocrine disorders or inflammation), disorders of accessory glands, coital disorders, exposure to diethylstilbestrol (DES) a synthetic estrogen used in the 1950's and 1960's that caused cysts in the male reproductive tract, undescended testicles, and in rare cases genetic disorders such as a chromosomal abnormality.

Contributing factors to the development of testosterone deficiency include:

Medications, especially those used to treat depression or mental disorders;

Alcoholism;

Chemotherapy or radiation treatment for cancer that targets or harms the testicles;

Chronic illness;

Dysfunction of the pituitary gland (a gland in the brain that produces substances that regulate hormone production from the brain to the testis);

Hemochromatosis (too much iron in the blood);

Hypogonadism (when the testis is not able to produce high enough levels of testosterone, aka androgen deficiency, or sperm, aka spermatogenesis);

Inflammatory diseases, such as sarcoidosis (a condition that causes injury to or infection of the testicles);

Illnesses, such as AIDS, that compromise the immune system;

Excessive stress, which taxes the adrenal system.

Female infertility can also be caused by a variety of problems. Some of the more common disorders are Polycystic Ovarian Disease, Pelvic Inflammatory Disease, Ovulatory Dysfunction, Uterine Fibroids, Endometriosis, and Immunological Infertility.

Disorders of carbohydrate metabolism occur in many forms. The most common disorders are acquired. Acquired or secondary derangements in carbohydrate metabolism, such as diabetic ketoacidosis, hyperosmolar coma, and hypoglycemia, all affect the central nervous system. Many forms and variants of peripheral nerve disease also are seen in diabetes. The remaining disorders of carbohydrate metabolism are the rare inborn errors of metabolism (i.e. genetic defects).

The acquired disorders of carbohydrate metabolism are fairly common, both in the United States and internationally. Hypoglycemia is a common cause of neurological disease, especially acute mental deterioration, memory loss, disorientation, obtundation, and coma, among both alcoholics and patients with diabetes who are treated with insulin. Hyperinsulinemia from other causes is rare, but pancreatic tumors could be the cause. Diabetes, with its various neurological complications, is among the most common disorders treated in adult patients.

Diabetes (Diabetes mellitus) is the most common endocrine disease, and is characterized by abnormalities of glucose metabolism. The abnormal glucose metabolism associated with this disease results in hyperglycemia (high blood glucose levels) and eventually causes complications of multiple organ systems, including eyes, kidneys, nerves, and blood vessels. Patients with persistent hyperglycemia or abnormal glucose tolerance are generally diagnosed with the disease, although most commonly patients initially present with excessive urination (polyuria) and frequent drinking due to extreme thirst (polydipsia). These typical initial symptoms result from the osmotic effects of hyperglycemia.

The pathogenesis of diabetes mellitus is typically associated with pancreatic dysfunction, particularly of the beta cells of the pancreatic islets of Langerhans. This dysfunction may lead to destruction of the islet beta cells, which produce insulin, a glucose regulatory peptide hormone. Diabetes mellitus has been generally categorized as insulin dependent or type I, versus non-insulin dependent, or type II.

The principal three forms or diabetes are:

Type I: Results from the body's failure to produce insulin. Treatment usually involves insulin administration.

Type II: Results from a condition in which the body fails to use insulin properly, combined with relative insulin deficiency. Many people destined to develop type II diabetes spend many years in a state of Pre-diabetes, a condition that occurs when a person's blood glucose levels are higher than normal but not high enough for a diagnosis of type II diabetes.

Gestational diabetes: Pregnant women who have never had diabetes before but who have high blood sugar (glucose) levels during pregnancy are said to have gestational diabetes. Gestational diabetes affects about 4% of all pregnant women. It may precede development of type II (or rarely type I).

Many other forms of diabetes are categorized separately from these. Examples include congenital diabetes due to genetic defects of insulin secretion, cystic fibrosis-related diabetes, steroid diabetes induced by high doses of glucocorticoids, and several forms of monogenic diabetes.

However, this terminology has evolved as the disease has become better understood. For example, it has been found that in some patients suffering from non-insulin dependent diabetes, the disease progresses into an insulin dependent form, while in other patients insulin dependence does not develop.

Patients are thus often categorized in terms of the mechanisms of pathogenesis of islet destruction, and the designation type I is now used to refer to autoimmune islet pathogenesis, i.e., to diabetes caused by islet-specific autoimmune attack, and is so used herein. The term insulin dependent diabetes mellitus (IDDM) refers to Type I diabetes that has progressed to a stage where enough autoimmune destruction of the pancreatic beta cells has occurred to produce overt symptoms. The term pre-IDDM refers to an autoimmune condition that can be detected by biopsy or by analysis of autoimmune responses, in which pancreatic islet beta cells are being subject to a specific autoimmune attack to an extent where some cells may be subject to destruction. In pre-IDDM, however, the destruction (if any) has not progressed to an extent sufficient to require the administration of insulin. Since there can be a point in the early stages of Type I diabetes in which overt symptoms are observed but some islet function remains (known as the "honeymoon period", not all Type I diabetes is classified as IDDM, and not all pre-IDDM presents without overt symptoms.

The metabolic complications associated with the abnormal metabolism caused by insulin insufficiency can affect numerous organ systems. The most common acute metabolic complication is that of diabetic ketoacidosis, characterized by severe hyperglycemia (and resulting hypovolemia caused by osmotic diuresis) as well as metabolic acidosis induced by excess free fatty acid release and the production of ketone bodies.

In addition to the acute metabolic complication of ketoacidosis, the diabetic patient is susceptible to a series of late complications that cause considerable morbidity and premature mortality. Atherosclerosis occurs more extensively and earlier in diabetics than in the general population as a result of abnormalities in both glucose and lipid metabolism. This vascular pathology can lead to, inter alia, coronary artery disease, stroke, and peripheral vascular disease with gangrene. Retinopathy is another vascular complication of diabetes. Diabetic retinopathy is a leading cause of blindness, and is initiated by increased permeability of retinal capillaries which can progress to occlusion, hemorrhage, aneurysm formation, and neovascularization known as proliferative retinopathy.

As mentioned above, meticulous control of blood glucose has been associated with amelioration of the late complications of Type I diabetes, suggesting that preservation or restoration of beta cell function could reduce or eliminate the majority of the pathologic complications of the disease.

The inherited disorders of carbohydrate metabolism are rare. Severe defects of the pyruvate dehydrogenase (PDH) complex and the benign chemical anomaly called pentosuria have been reported in very few (2-6) patients.

Hypoglycemia, diabetic ketoacidosis, and hyperosmolar coma are all potentially fatal but potentially curable conditions.

In the present study, the present inventors have discovered novel secreted proteins, namely PRT5, PRT6, PRT7 and PRT8, which are the object of the present invention. The present invention also provides compositions comprising said proteins, as well as their uses in therapeutics. The antibodies which specifically recognize the novel proteins described herein are also an object of the present invention, as well as their uses in diagnosis and treatment.

Furthermore, it has been surprisingly found by the inventor that a shortened PRT8 peptide, namely sbPRT8, has an improved biological activity over the full length PRT8 peptide, and is able to lower blood glucose level, even more significantly.

These and other uses and objects of the invention will become apparent as the description proceeds.

SUMMARY OF THE INVENTION

It is an object of the present invention to provide an isolated polypeptide comprising (a) the amino acid sequence set forth in SEQ ID NO: 21; or (b) an amino acid sequence that is at least 95% identical to SEQ ID NO: 21. In a specific embodiment, the isolated polypeptide consists of the amino acid sequence set forth in SEQ ID NO: 21. In another specific embodiment, the polypeptide is modified at the N-terminal end with an acetyl moiety and at the C-terminal end with an amide moiety.

The invention further provides a pharmaceutical composition comprising an isolated polypeptide as defined above and at least one pharmaceutically acceptable carrier, excipient, or diluent.

The invention further provides a method for lowering the blood glucose level in a subject, said method comprising administering a therapeutically effective amount of the polypeptide as described above to said subject. In some specific embodiments, said subject suffers from a disease or disorder associated with hyperglycemia. Such disease or disorder may be selected, but is not limited to, diabetes mellitus type 1, diabetes mellitus type 2, nephropathy, retinopathy, cardiovascular diseases, glands dysfunction, pancreas diseases, sepsis, intracranial diseases, and post-surgery stress.

The invention still further provides a method for lowering plasma triglycerides (TG) blood level in a subject, said method comprising administering a therapeutically effective amount of the polypeptide as described above to said subject.

The invention further provides a method for lowering the level of glycated hemoglobin (HbA1c) in blood, said method comprising administering a therapeutically effective amount of the polypeptide of claim 1 as described above to said subject.

The invention further provides an isolated nucleic acid molecule encoding a polypeptide comprising (a) the amino acid sequence set forth in SEQ ID NO: 21; or (b) an amino acid sequence that is at least 95% identical to SEQ ID NO: 21, an expression vector comprising the same, and a host cell comprising said expression vector.

It is a further object of the invention to provide an isolated polypeptide comprising an amino acid sequence denoted by any one of SEQ. ID. NO. 1, SEQ. ID. NO. 2, SEQ. ID. NO. 3, or SEQ. ID. NO. 4, and any fragments, derivatives or analogs thereof. Said polypeptide is a chemokine-like secreted protein, and is also referred to herein as PRT5, PRT6, PRT7, or PRT8, respectively.

Similarly, it is an object of the present invention to provide an isolated protein comprising any one of the isolated polypeptide PRT5, PRT6, PRT7, or PRT8, and any fragments, derivatives or analogs thereof.

It is a further object of the present invention to provide an isolated nucleic acid molecule comprising a sequence encoding any one of the isolated polypeptide PRT5, PRT6, PRT7, or PRT8 and any fragments, derivatives, and analogs thereof.

It is a further object of the present invention to provide a vector comprising the isolated nucleic acid molecule encoding any one of the isolated polypeptide PRT5, PRT6, PRT7, or PRT8, wherein said nucleic acid molecule is operably linked to a promoter and said vector is an expression vector. In addition, a cell comprising said vector is also provided by the present invention.

It is another further object of the present invention to provide composition comprising any one of the isolated polypeptide PRT5, PRT6, PRT7, or PRT8, and any fragments, derivatives or analogs thereof, or a protein comprising thereof. Said composition may further comprise a pharmaceutically acceptable carrier, excipient, or diluent.

Said composition provided by the invention, when comprising PRT5 or PRT8, or biologically active fragments or derivatives thereof, may have specific therapeutic uses, such as enhancing glucose metabolism, inducing insulin receptor expression, inducing the translocation of Glut-4 transporter to the plasma membrane, inducing glucose influx and/or glycogen synthesis, and inducing glycolysis and fatty acid synthesis, or said composition may be used for the treatment of a disorder selected from the group consisting of glucose metabolism-related disorders, diabetes, metabolic syndrome, obesity, endocrine diseases, and muscle disorders.

Said composition provided by the invention, when comprising PRT6, or biologically active fragments or derivatives thereof, may have specific therapeutic uses, such as enhancing testosterone production, or may be used for the treatment of testosterone deficiency or low testosterone-related disorders.

Alternatively, said composition provided by the invention, when comprising PRT7, or biologically active fragments or derivatives thereof, may have specific effects, such as inducing p53 expression, apoptosis or cell death, or it has a therapeutic use in the treatment of cancer.

It is another further object of the present invention to provide the use of any one of the isolated polypeptides PRT5, PRT6, PRT7, or PRT8 described in the invention in the preparation of a medicament for the treatment of a disease or disorder, said disease or disorder being selected from the group consisting of diseases that have an immunological component or etiology, infectious diseases, acute and chronic inflammatory diseases, cancer, transplantation and autoimmune diseases, diseases linked to fertility and disorders of carbohydrate metabolism, diabetes, metabolic syndrome, obesity, endocrine diseases, and muscle disorders.

It is a yet further object of the present invention to provide a method for the treatment of a disease or disorder in a subject in need thereof, comprising administering a therapeutic effective amount of the isolated polypeptide PRT5, PRT6, PRT7, or PRT8, or the protein comprising the same, or a composition comprising thereof, to said subject, said disease or disorder being selected from the group consisting of diseases that have an immunological component or etiology, infectious diseases, acute and chronic inflammatory diseases, cancer, transplantation and autoimmune diseases, diseases linked to fertility, disorders of carbohydrate metabolism, diabetes, metabolic syndrome, obesity, endocrine diseases, and muscle disorders.

It is a yet further object of the present invention to provide an antibody, or any fragments or derivatives thereof, said antibody being able to specifically recognize one of the isolated polypeptides PRT5, PRT6, PRT7, or PRT8, or a fragment or derivative thereof, or protein comprising the same. The present invention also provides compositions comprising the anti-PRT5, anti-PRT6, anti-PRT7, or anti-PRT8 antibodies, and their therapeutic and diagnostic uses.

Lastly, the present invention provides a diagnostic kit for the diagnosis and/or the monitoring of treatment efficacy and/or for assessing the prognosis of a disease or disorder, said disease or disorder being selected from the group consisting of diseases that have an immunological component or etiology, infectious diseases, acute and chronic inflammatory diseases, cancer, transplantation and autoimmune diseases, diseases linked to fertility and disorders of carbohydrate metabolism, said kit comprising at least one of the anti-PRT5, anti-PRT6, anti-PRT7, or anti-PRT8 antibodies or a composition comprising thereof; and instructions for carrying out the detection of the presence of an antigen in a sample, wherein said antigen is specifically recognized by said antibody. Said kit may further comprising at least one of the following components: at least one means for collecting a sample to be tested; at least one reagent necessary for detection of said recognition of said antigen by said antibody; and at least one control sample.

BRIEF DESCRIPTION OF THE FIGURES

FIG. 1A: Graph showing glucose concentration (mg/dL) in the blood of C57B1 mice injected with 2 mg/kg of glucose, and measured 1 day post-PRT5 injection, at time points 0.5, 1.5, 2, 2.5 and 4 hours (hr).

FIG. 1B: Graph showing glucose concentration (mg/dL) in the blood of C57B1 mice injected with 2 mg/kg of glucose, and measured 2 days post-PRT5 injection, at time points 0.5, 1 and 2 hours (hr).

FIG. 1C: Graph showing glucose concentration (mg/dL) in the blood of C57B1 mice injected with 2 mg/kg of glucose, and measured 3 days post-PRT5 injection, at time points 0.5, 1 and 2 hours (hr).

FIG. 1D: Graph showing glucose concentration (mg/dL) in the blood of C57B1 mice injected with 2 mg/kg of glucose, and measured 4 days post-PRT5 injection, at time points 0.5, 1 and 2 hours (hr).

Legend: -◇- Saline; -■- 1 µg/kg PRT5; -▲- 5 µg/kg PRT5; Sal.=saline; Gluc.=glucose; T.inj.=Time after glucose injection.

Figure 1A:
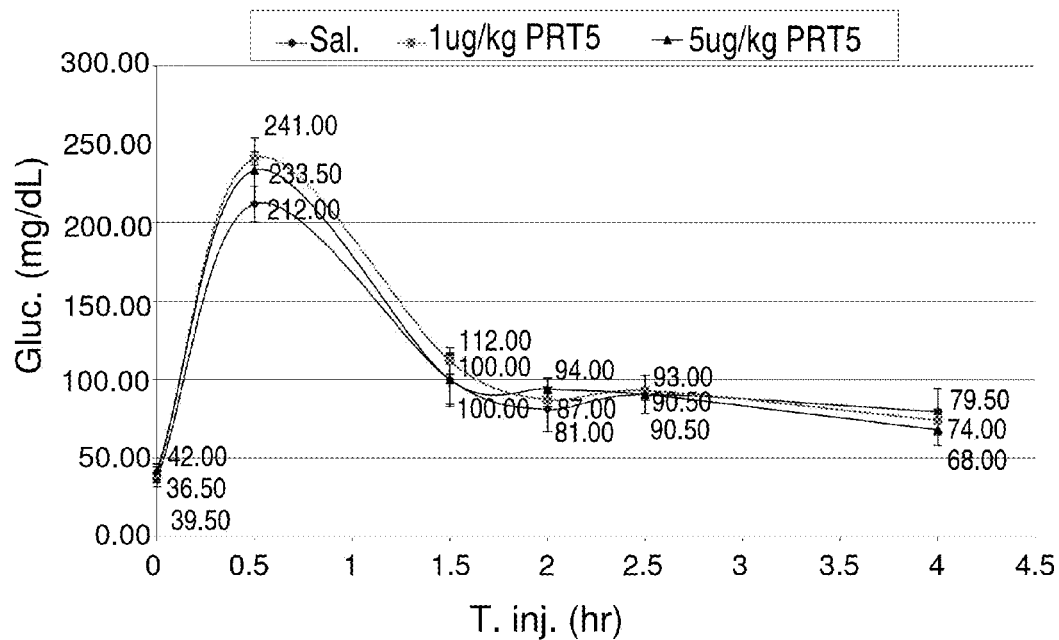
FIGS. 1A-1D: Effect of PRT5 on glucose levels
Figure 1B:
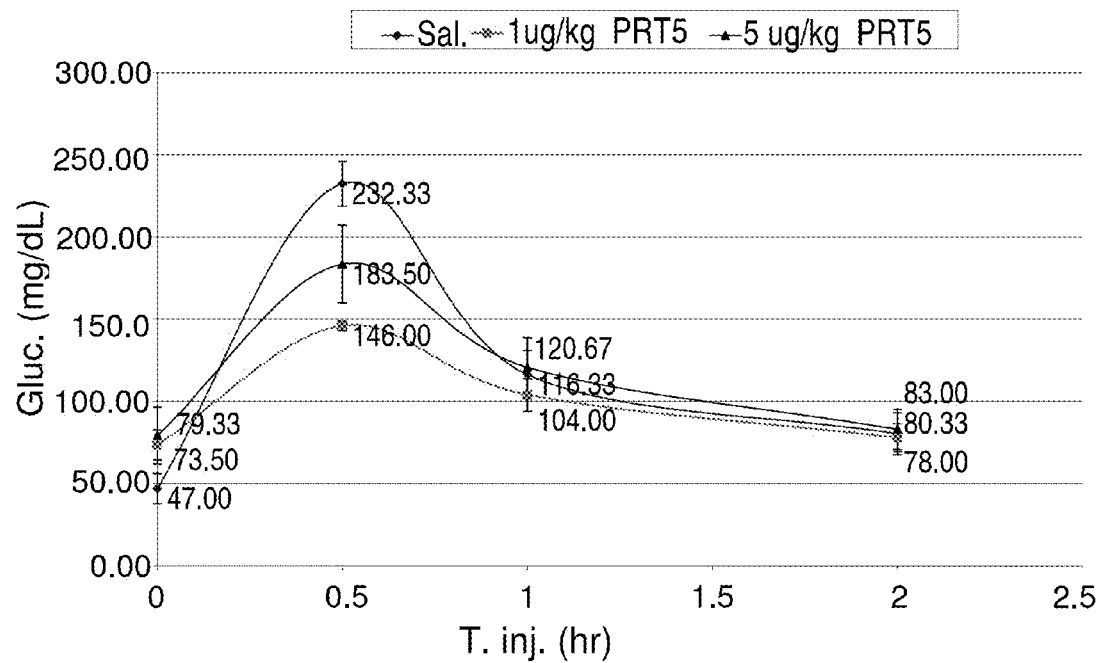
Figure 1C:
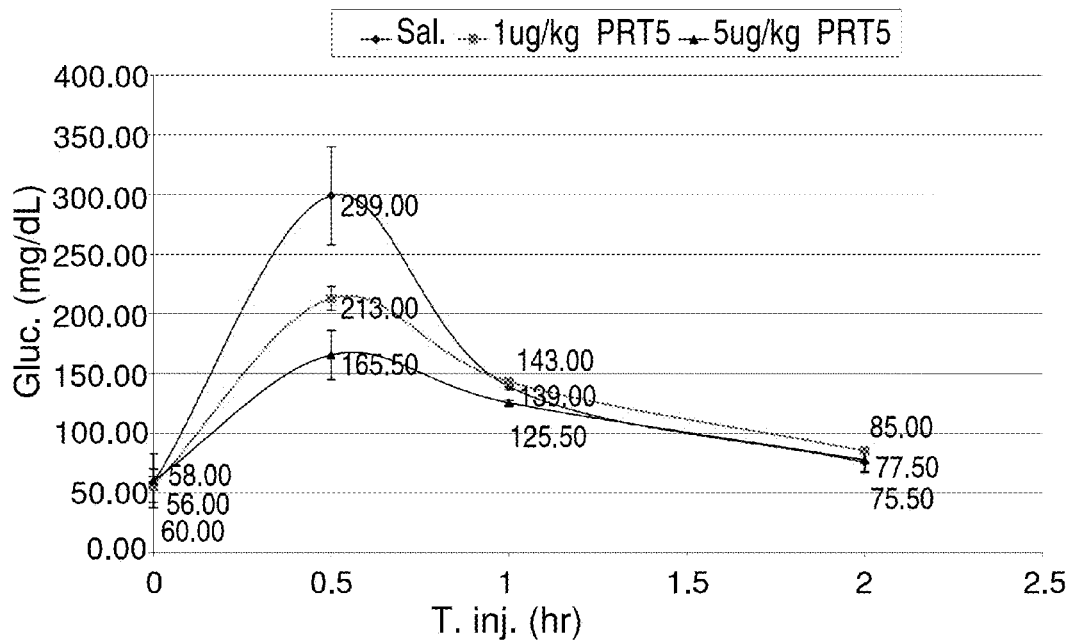
Figure 1D:
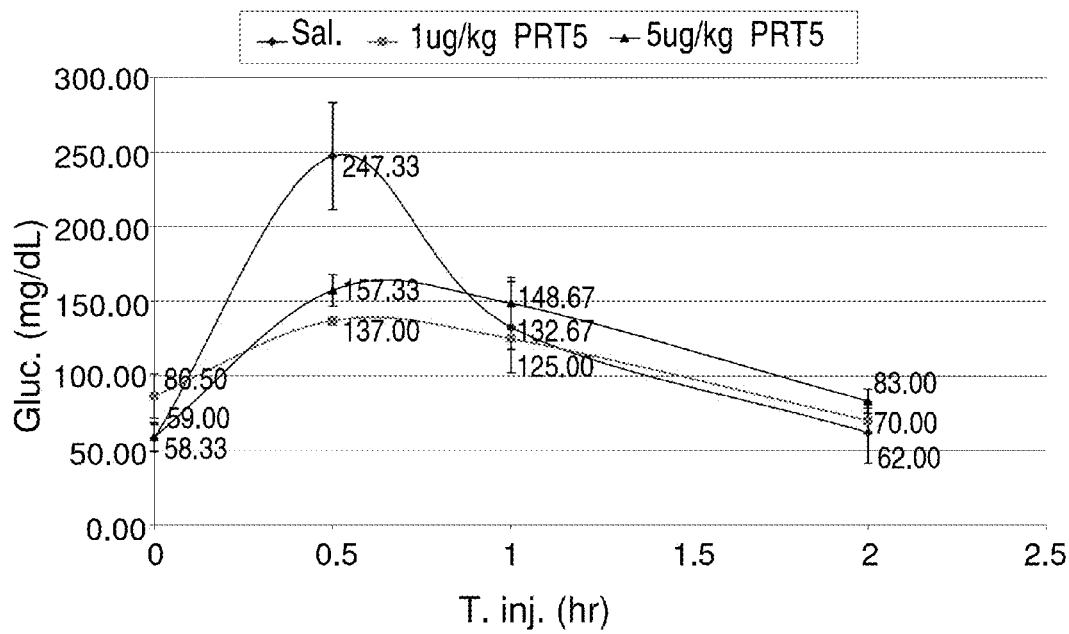
Figure 2A:
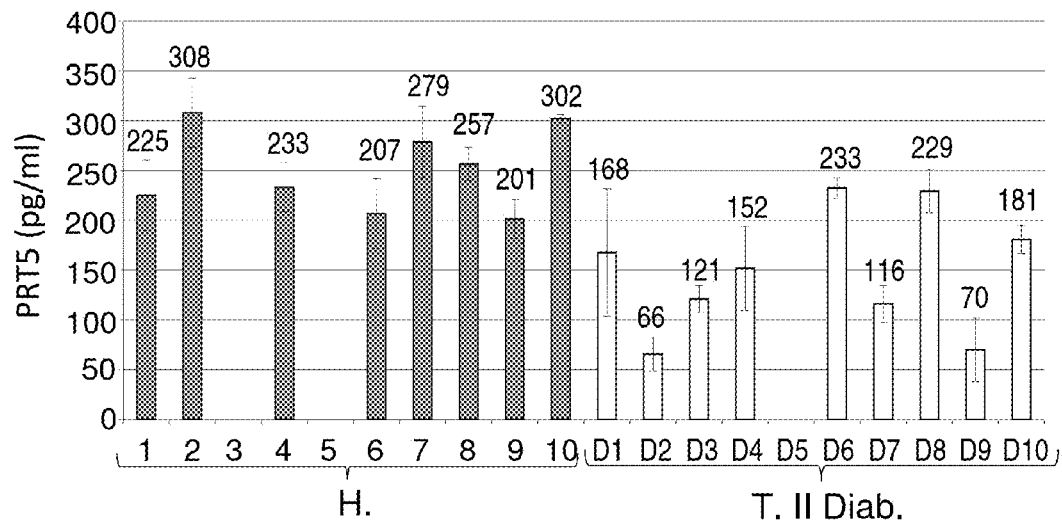
Figure 2B:
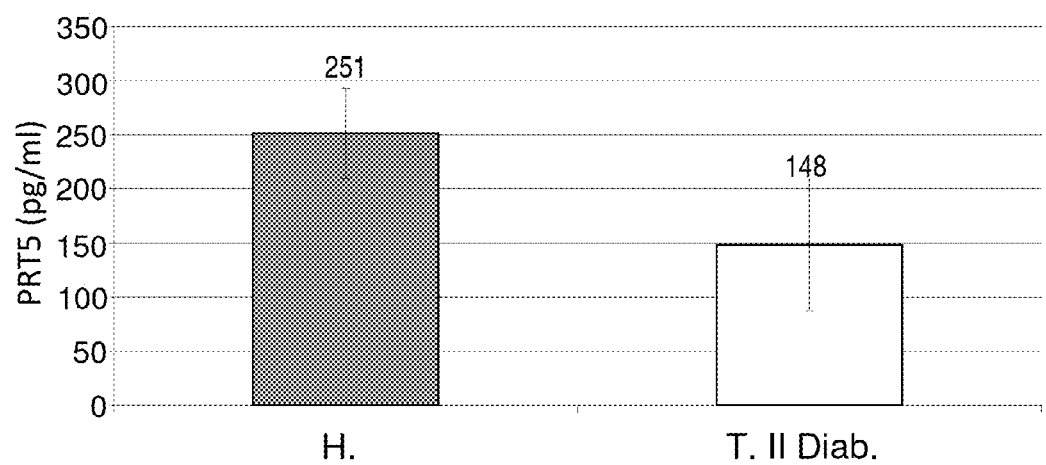

FIGS. 2A-2B: PRT5 levels in human blood serum from healthy individuals and diabetes patients FIG. 2A: Histogram showing the levels of PRT5 (pg/ml) in 8 healthy individuals and 9 type II Diabetes patients. Samples were diluted 1:3 and anti-PRT5 antibody was diluted 1:250.

FIG. 2B: Histogram showing the levels of PRT5 (pg/ml) in healthy individuals versus type II Diabetes patients (average of 10 samples each). Samples were diluted 1:3 and anti-PRT5 antibody was diluted 1:250.

Legend: H.=healthy; T.II Diab.=Type II Diabetes.

Figure 3A:
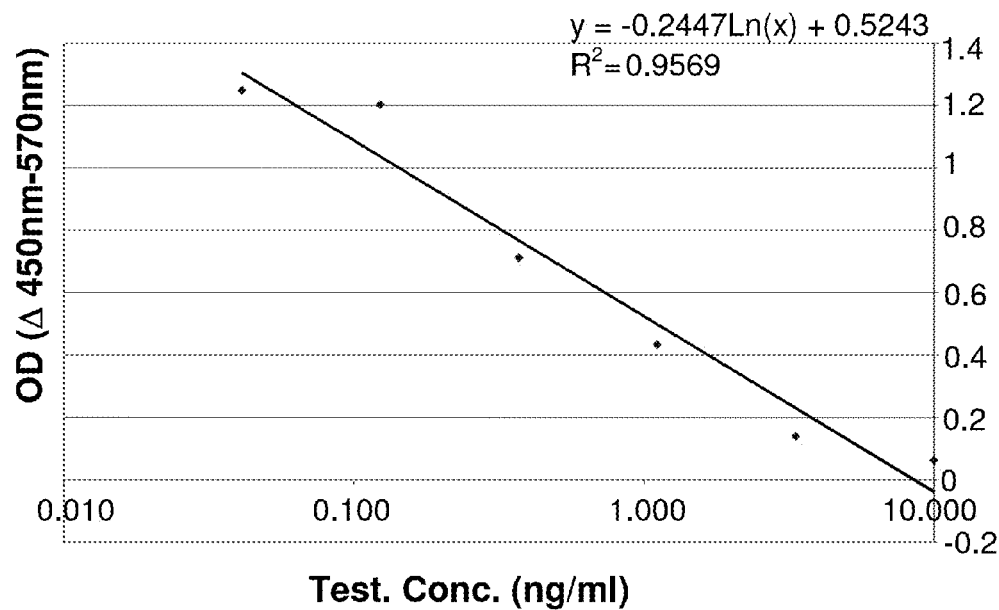
Figure 3B:
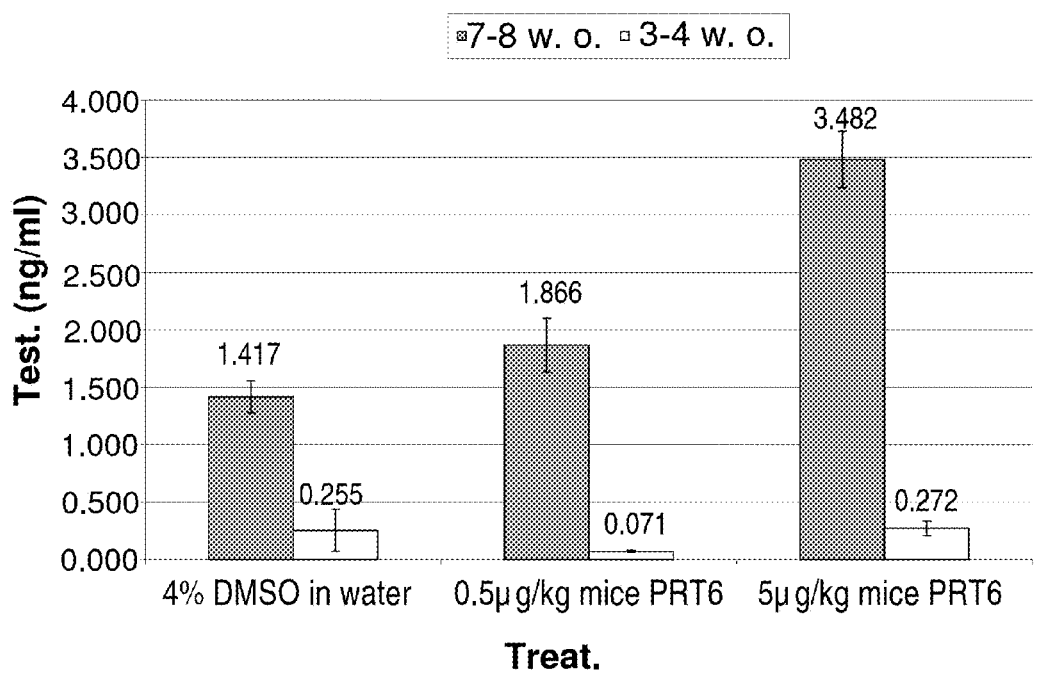

FIGS. 3A-3B: Effect of PRT6 on testosterone levels

FIG. 3A: Testosterone calibration curve.

FIG. 3B: Histogram showing levels of testosterone (ng/ml) in blood serum (blood diluted 1:10) of mice treated for 4 days with 4% DMSO in water, 0.5 µg/kg of PRT6, or 5 µg/kg of PRT6 (6 mice per group).

Legend: Test. conc.=testosterone concentration; Test.=testosterone; Treat.=treatment; w.o.=weeks old.

FIGS. 4A-4F: PRT7 levels in pancreatic and lung cancer patients

Figure 4A:
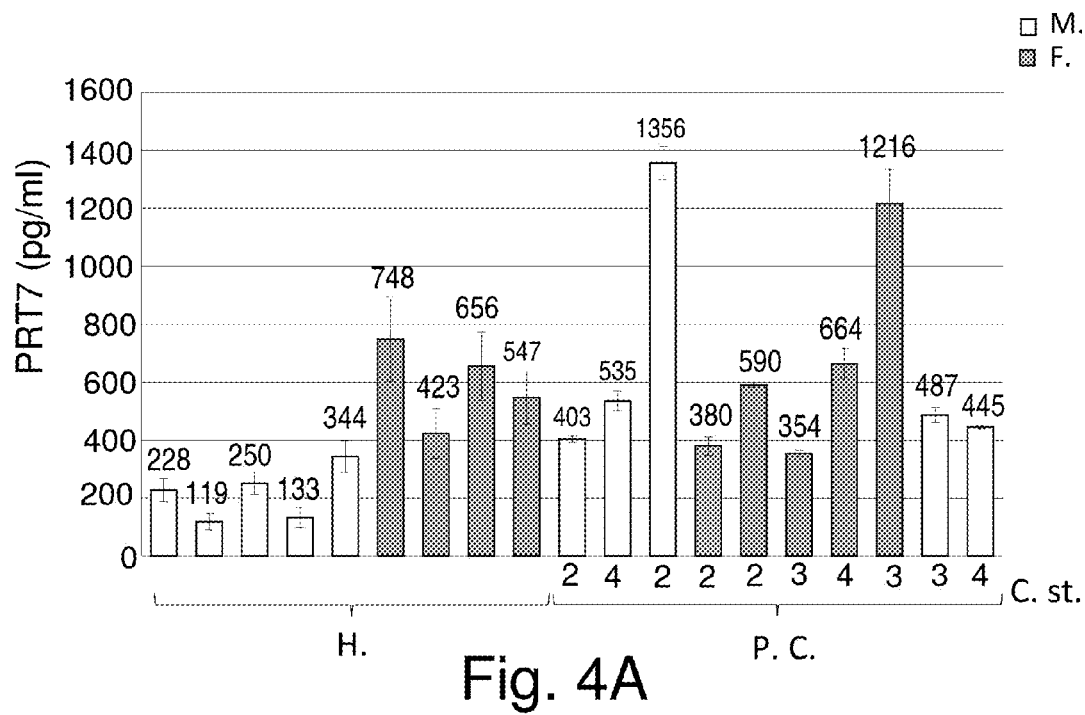

FIG. 4A: Histogram showing the levels of PRT7 (pg/ml) in pancreatic cancer patients (10 patients, cancer stage indicated below each column) compared to healthy individuals (9 samples).

Figure 4B:
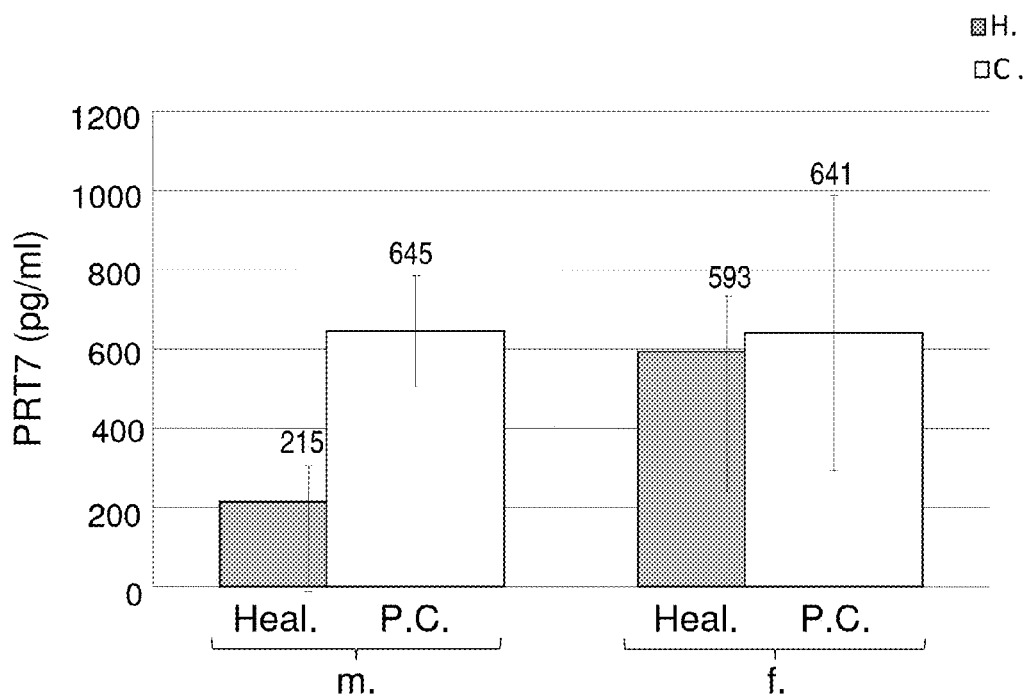

FIG. 4B: Histogram showing the average level of PRT7 (pg/ml) in pancreatic cancer patients versus healthy individuals, in males and females respectively.

Figure 4C:
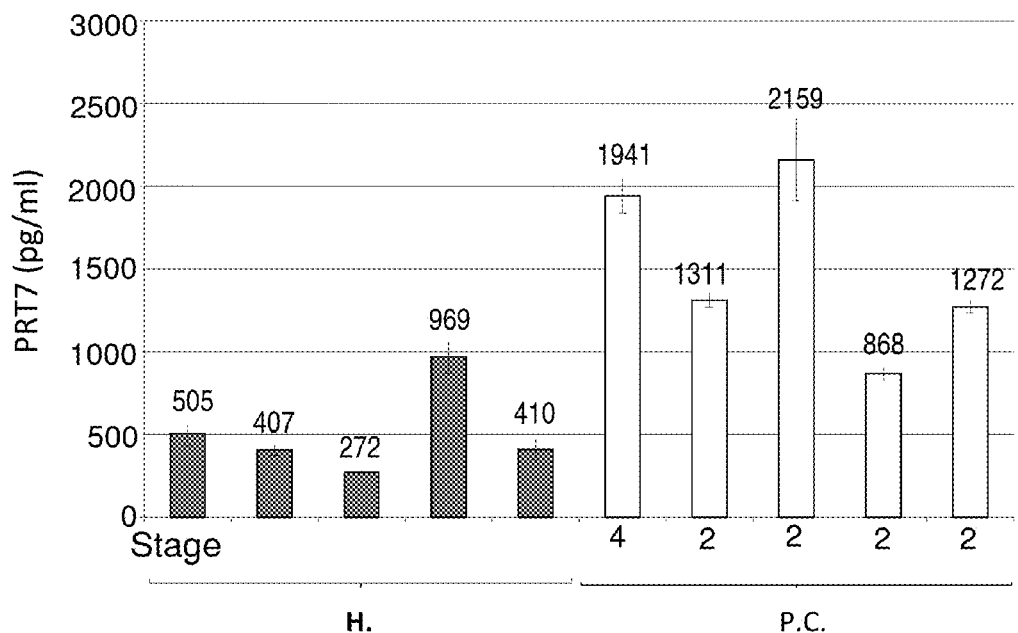

FIG. 4C: Histogram showing the levels of PRT7 (pg/ml) in samples from males only, in pancreatic cancer patients (5 patients, cancer stage indicated below each column) compared to healthy individuals (5 samples).

Figure 4D:
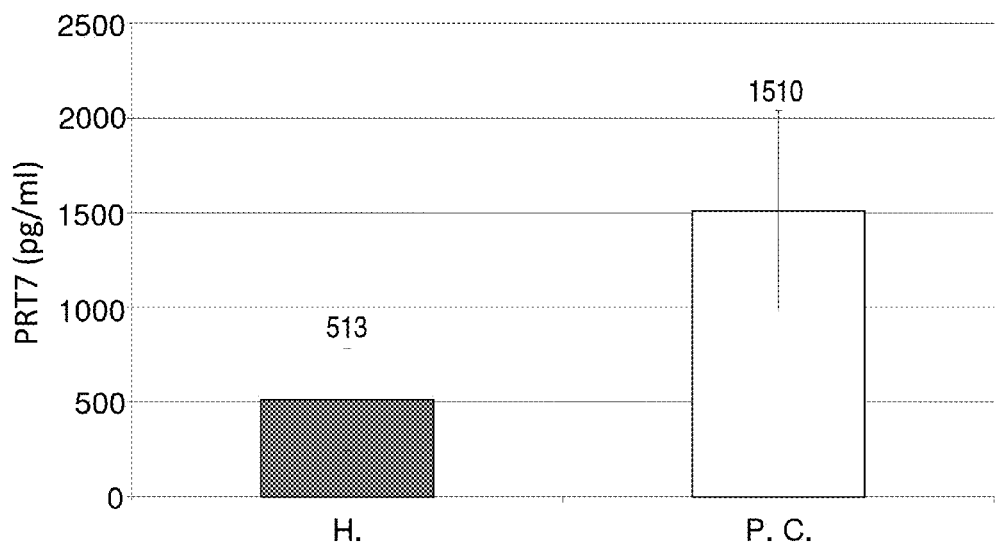

FIG. 4D: Histogram showing the average level of PRT7 levels (pg/ml) in pancreatic cancer patients versus healthy individuals, in males only.

Figure 4E:
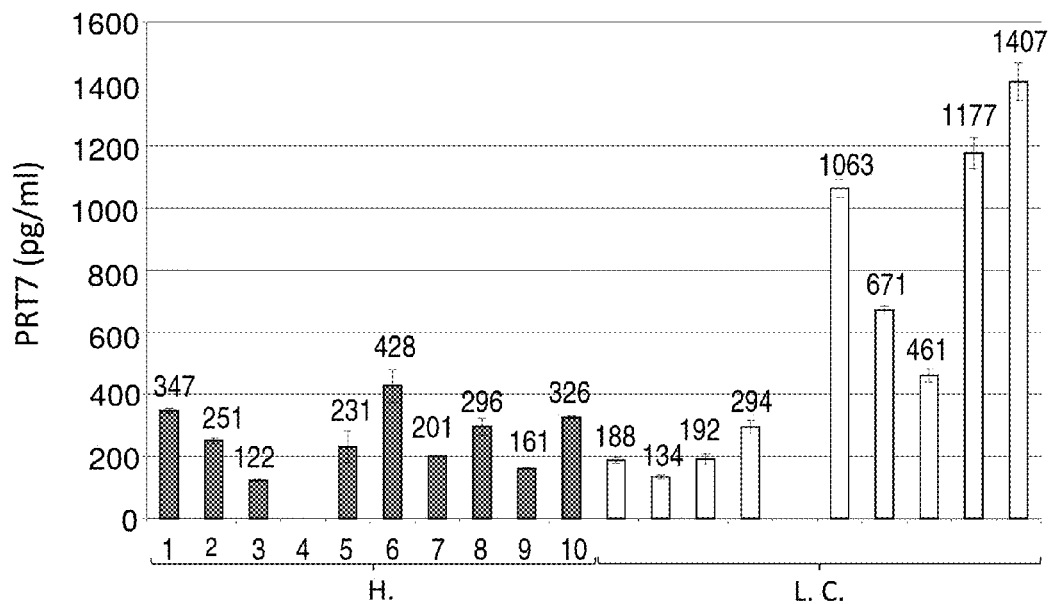

FIG. 4E: Histogram showing the levels of PRT7 (pg/ml) in lung cancer patients (9 samples) compared to healthy individuals (9 samples).

Figure 4F:
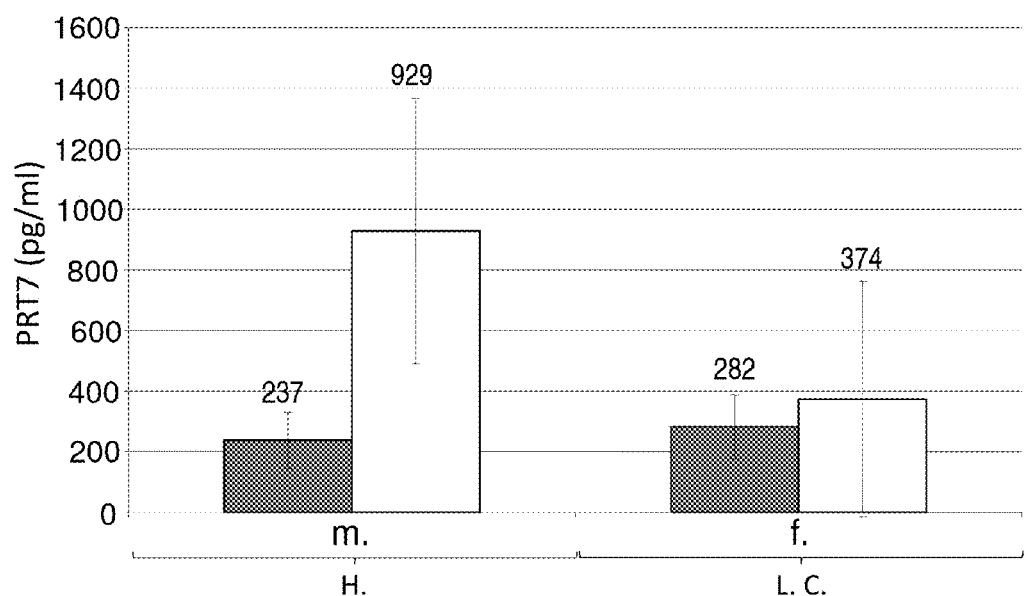

FIG. 4F: Histogram showing the average level of PRT7 (pg/ml) in lung cancer patients versus healthy individuals, in males and females respectively.

Legend: H.=healthy; PC=Pancreatic Cancer; C. st.=cancer stage; LC=Lung Cancer; m.=male; f.=female.

Figure 5A:
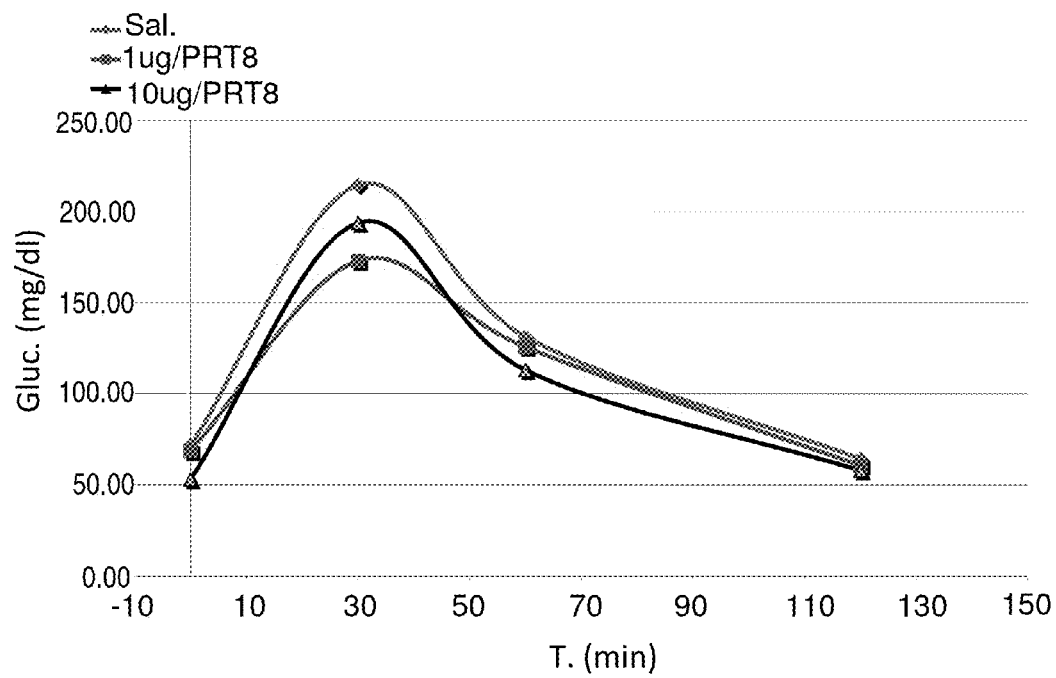
Figure 5B:
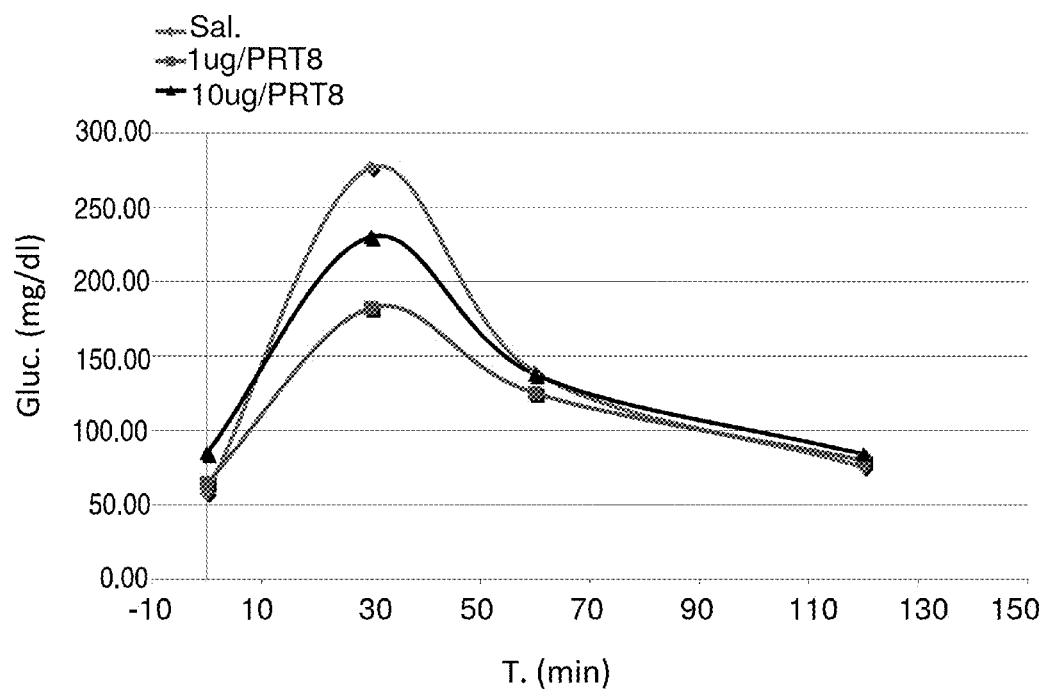

FIGS. 5A-5B: Effect of PRT8 on glucose levels

FIG. 5A: Graph showing glucose levels in C57B1 mice injected with 2 mg/kg of glucose, measured 2 days post-PRT8 injection, at time points 30, 60, and 120 minutes.

FIG. 5B: Graph showing glucose levels in C57B1 mice injected with 2 mg/kg of glucose, measured 3 days post-PRT8 injection, at time points 30, 60, and 120 minutes. Legend: -◇- Saline; -■- 1 µg/kg PRT8; -▲- 10 µg/kg PRT8; Sal.=saline; Gluc.=glucose; T.=Time after glucose injection.

Figure 6A:
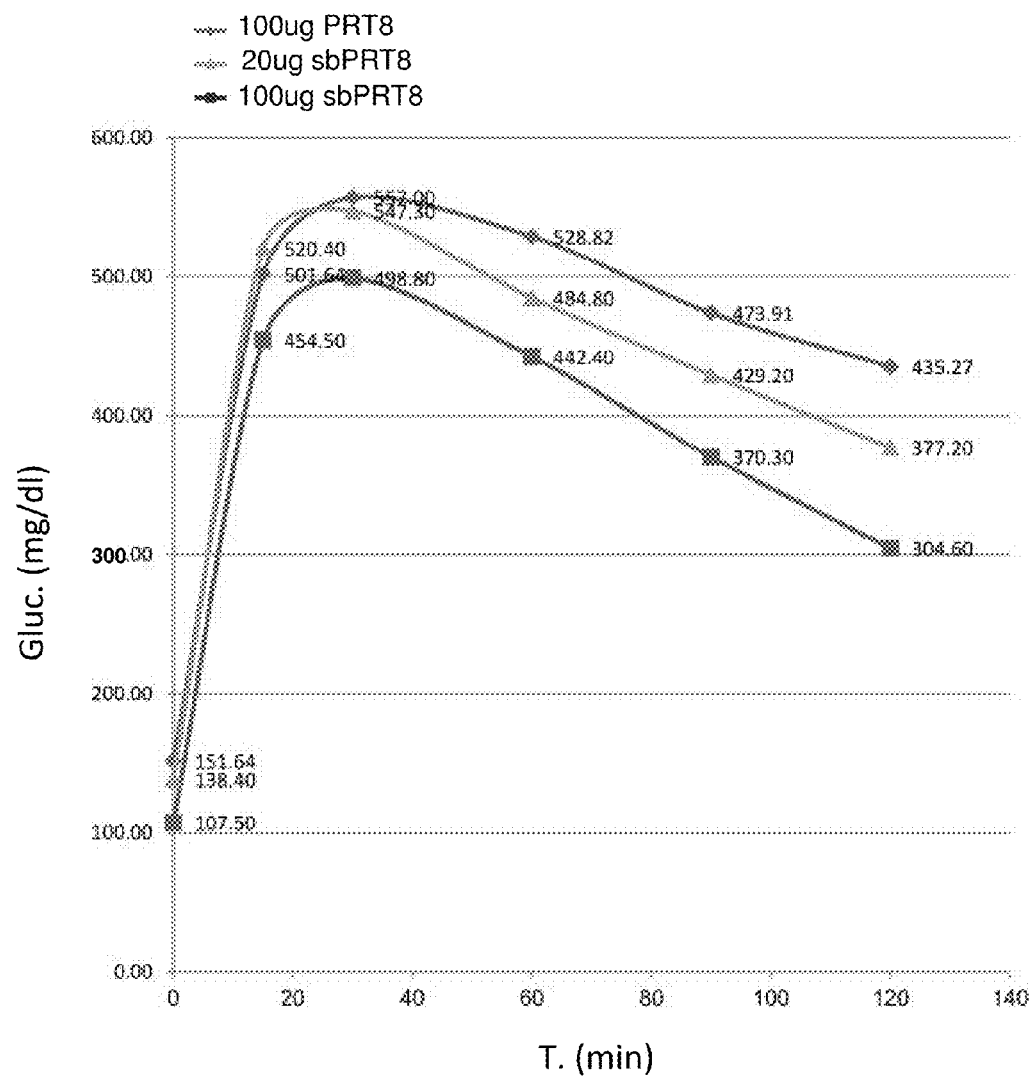
Figure 6B:
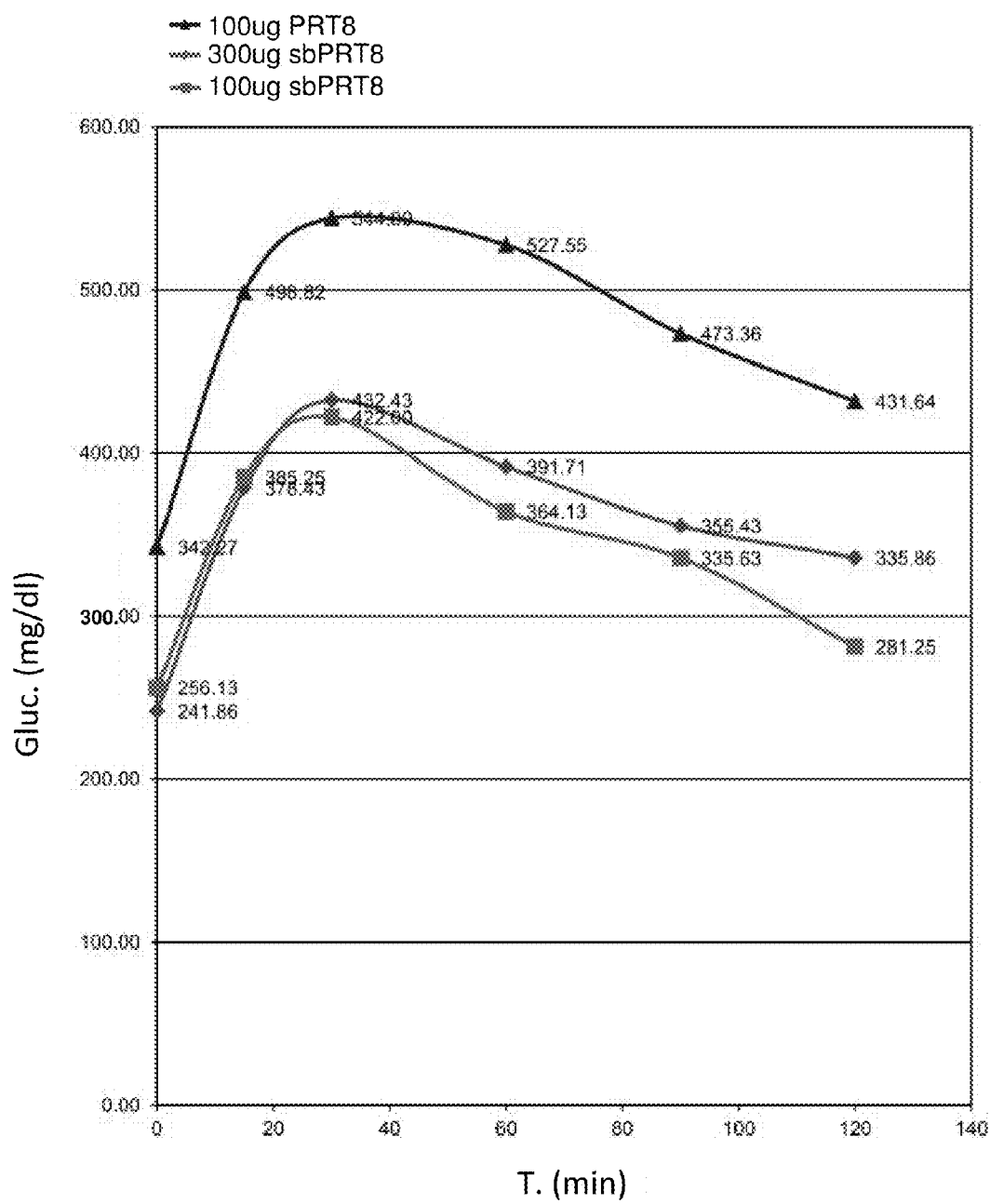

FIGS. 6A-6B: Effects of sbPRT8 on C57B1/6 mice treated with streptozotocyn (STZ)

FIG. 6A: Graph showing glucose levels in C57B1/6 mice injected with STZ (IP injection of 50 mg/kg for 4 days) followed by a 5 weeks treatment with either PRT8 or sbPRT8, and IP injected with 1 mg/kg of glucose (IPGTT);

Legend: -♦- 100 µg/mice of PRT8; -▲- 20 µg/mice of sbPRT8; -■- 100 µg/mice sbPRT8; Gluc.=glucose; T.=Time after glucose injection FIG. 6B: Graph showing glucose levels in C57B1/6 mice injected with STZ (IP injection of 50 mg/kg for 4 days) followed by a 4 weeks treatment with either PRT8 or sbPRT8, and IP injected with 1 mg/kg of glucose (IPGTT);

Legend: -▲- 100 µg/mice PRT8; -■- 100 µg/mice sbPRT8; -♦- 300 µg/mice of SbPRT8.

DETAILED DESCRIPTION OF THE INVENTION

The present inventors have isolated novel proteins, all of which comprising at least one signal peptide domain, indicating that these are secreted, or chemokine-like proteins.

Polypeptide sequence analysis thus indicated that the novel isolated proteins have structural characteristics resembling a chemokine, indicating that these are ligand-type or chemokine-type proteins.

These novel isolated proteins, which were named PRT5, PRT6, PRT7 and PRT8, are the object of the present invention. All polypeptides referred to herein present a prominent signal peptide sequence as checked by free domain software (SignalP from CBS, Center for Biological Sequence Analysis, Technical University of Denmark) and by a software developed in-house (data not shown).

The expression pattern of the different proteins is presented herein below in the Examples. Briefly, PRT5 was found particularly in the pancreas and in testis, and also in spleen, ovary and small intestine (Example 1). PRT6 was found particularly in the testis (Example 4). PRT7 was found particularly in fetal brain, and also in liver, skeletal muscle and adult brain (Example 6). Lastly, PRT8 was found particularly in the pancreas and testis, and also in the liver (Example 8).

Sequence comparison did not show homology between the newly-identified proteins and any other protein described to date.

Thus, in a first aspect, the present invention provides an isolated polypeptide being characterized as a chemokine-like secreted protein, said polypeptide comprising an amino acid sequence denoted by any one of SEQ ID NO. 1, SEQ ID NO. 2, SEQ ID NO. 3, and SEQ ID NO. 4 as well as fragments, analogs and derivatives thereof.

The term "polypeptide" is used herein to denote a polypeptide or a protein. The polypeptide may be obtained synthetically, through genetic engineering methods, expression in a host cell, or through any other suitable means.

In some embodiments, the polypeptide of the invention is modified at the C-terminal end and/or at the N-terminal end. In one specific embodiment, the peptide is modified as follows: acetyl-(Peptide Sequence)-amide. In some other specific embodiments, the polypeptide of the invention is modified with one or more groups selected from a biotin group, a fluorescent group or a cysteine residue.

In the literature, the term "protein" is generally used to refer to the complete biological molecule in a stable conformation, as well as to its modifications. Polypeptide can refer to any single linear chain of amino acids, usually regardless of length, but often implies an absence of a defined conformation.

Thus, the present invention refers both to the polypeptides as well as to the proteins comprising the amino acid sequence denoted by SEQ ID NO. 1, SEQ ID NO. 2, SEQ ID NO. 3, and SEQ ID NO. 4, as well as fragments, analogs and derivatives thereof.

Unless indicated otherwise, a polypeptide is generally composed of naturally-occurring L-amino acids.

The term "biological characteristics", with respect to a polypeptide molecule, refers to the polypeptide's ability to exert at least one of the in vitro or in vivo effects that may be exerted by the full PRT5, PRT6, PRT7 or PRT8 polypeptide, including but not limited to the biological activities described in the specification. For example, biological characteristics include the ability to treat cancer, immune system associated diseases, viral diseases and inflammatory diseases.

The term "without significantly affecting the biological characteristics of the modified molecule as compared to the unmodified molecule" means to denote that the modified molecule retains a biological activity qualitatively similar to that of the unmodified molecule.

With respect to a modified polypeptide, in connection with the present invention, it is understood that it retains at least one of the biological characteristics of a protein having the amino acid sequence selected from the group consisting of SEQ. ID. NO. 1, SEQ. ID. NO. 2, SEQ. ID. NO. 3, and SEQ. ID. NO. 4. In order to determine whether a polypeptide retains a biological activity qualitatively similar to that of the unmodified molecule, one or more assays can be carried out, such as for example an in vitro, in vivo or a clinical experiment in which a modified polypeptide is compared to the corresponding unmodified one (namely PRT5, PRT6, PRT7 or PRT8 polypeptide, or a fragment thereof) that is assayed in parallel or in a separately conducted experiment.

A modified polypeptide may be a polypeptide that includes a contiguous sequence of at least 8, 12, 15, 20, 25, 30, 35, 40, 45, 50, 55, 60 or at least 65 amino acid residues that has a degree of identity to a corresponding sequence of at least 8, 12, 15, 20, 25, 30, 35, 40, 45, 50, 55, 60 or at least 65 amino acid residues included in the PRT5, PRT6, PRT7 or PRT8 polypeptide, the degree of identity being at least 70%, preferably at least 80%, more preferably at least 90% and particularly at least 95%.

Also provided by the invention are polypeptides derived from PRT5, PRT6, PRT7 or PRT8, e.g., modified polypeptides in which one or more amino acids are replaced by another amino acid by conservative substitution. As used herein, "conservative substitution" refers to the substitution of an amino acid in one class by an amino acid of the same class, where a class is defined by common physicochemical amino acid side chain properties and high substitution frequencies in homologous proteins found in nature. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu is a conservative substitution.

In one embodiment, only one substitution is made in the amino acid sequence. In another embodiment, two substitutions are made. In a further embodiment, three substitutions are made. The maximum number of substitutions should not exceed the number of amino acids which leaves at least 70%, desirably at least 80%, preferably at least 90%, most preferably at least 95% of the amino acids in the unsubstituted sequence. In one particular embodiment, the substitutions which include up to 3, at times up to 6 amino acid residues substituted by others, are conservative substitutions.

In a further embodiment, one or more amino acids may be replaced by D-amino acids, preferably the corresponding D-amino acids. In a particular embodiment, all of the amino acids are D-amino acids.

Thus, it is to be understood that the invention pertains to a protein or a polypeptide comprising a sequence homologous to the sequences disclosed herein with substantially equal or greater activity. A homologous sequence refers to a sequence having deletions, additions or substitutions to no more than 25% of the total amino acid number, preferably no more than 10%.

Preferred substitutions are changes that would not be expected to alter the secondary structure of the protein or polypeptide, i.e., conservative changes.

The following list shows amino acids (right side) that may be exchanged for the original amino acids (left side).

| Original Residue | Exemplary Substitution |
|---|---|
| Ala | Gly; Ser |
| Arg | Lys |
| Asn | Gln; His |
| Asp | Glu |
| Cys | Ser |
| Gln | Asn |

| Original Residue | Exemplary Substitution |
|---|---|
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Ser | Thr |
| Thr | Ser |
| Trp | Tyr |
| Tyr | Trp; Phe |
| Val | Ile; Leu |

Amino acids can also be grouped according to their essential features, such as charge, size of the side chain, and the like. The following list shows groups of similar amino acids. Preferred substitutions would exchange an amino acid present in one group with an amino acid from the same group, as follows:
1. Small aliphatic, nonpolar: Ala, Ser, Thr, Pro, Gly;
2. Polar negatively charged residues and their amides: Asp, Asn, Glu, Gln;
3. Polar positively charged residues: His, Arg, Lys;
4. Large aliphatic nonpolar residues: Met, Leu, Ile, Val, Cys;
5. Large aromatic residues: Phe, Tyr, Trp.

Further comments on amino acid substitutions and protein structure may be found in Schulz et al., Principles of Protein Structure, Springer-Verlag, New York, N.Y., 1979, and Creighton, T. E., Proteins: Structure and Molecular Properties, W.H. Freeman & Co., San Francisco, Calif. 1983.

The preferred conservative amino acid substitutions as detailed above are expected to substantially maintain or increase the function or activity of the protein of the invention, as detailed herein below. Of course, any amino acid substitutions, additions, or deletions are considered to be within the scope of the invention where the resulting protein or polypeptide retains its original functions. For example, a conservative substitution is one in which the polypeptide of the invention is still recognized by the antibodies which recognize the wild-type polypeptide.

The protein or polypeptide of the invention can be produced by conventional chemical methods, such as solid phase synthesis (using e.g. FMOC and BOC techniques), and solution phase synthesis. These proteins or polypeptides may also be produced in bacterial or insect cells or other eukaryotic transcriptional in vivo system, as detailed in the below-noted Current Protocols in Molecular Biology, Chapter 16. Following production, the protein or polypeptide are purified from the cells in which they have been produced. Polypeptide purification and isolation methods are known to the person of skill in the art and are detailed e.g., in Ausubel et al. (eds.) Current Protocols in Molecular Biology, Chapter 16, John Wiley and Sons, 2006 and in Coligan et al. (eds.). Current Protocols in Protein Science, Chapters 5 and 6, John Wiley and Sons, 2006. Advantageously, the protein or polypeptide may be produced as a fusion with a second protein, such as Glutathione-S-transferase (GST) or the like, or a sequence tag, such as the Histidine tag (His-tag) sequence. The use of fusion or tagged proteins simplifies the purification procedure, as detailed in the above-noted Current Protocols in Molecular Biology, Chapter 16, and in the instructions for His-tag protein expression and purification kits [available, e.g. from Qiagen GmbH, Germany].

The protein or polypeptide of the invention can also be synthesized in cell-free systems, using, for example, cell extracts or ribosomes.

The polypeptide or protein of the invention may be further modified to improve their function, affinity, or stability. For instance, cyclization may be used to impart greater stability and/or overall improved performance upon a polypeptide. A number of different cyclization methods have been developed, including side chain cyclization and backbone cyclization. These methods are well documented in the prior art [e.g. Yu et al., Bioorg. Med. Chem. 7, 161-75, 1999, Patel et al., J. Pept. Res. 53, 68-74, 1999, Valero et al., J. Pept. Res. 53, 56-67, 1999, Romanovskis et al., J. Pept. Res. 52, 356-74, 1998, Crozet et al. Mol. Divers. 3, 261-76, 1998, Rivier et al., J. Med. Chem. 41, 5012-9, 1998, Panzone et al., J. Antibiot. (Tokyo), 51, 872-9, 1998, Giblin et al., Proc. Natl. Acad. Sci. USA 95, 12814-8, 1998, Limal et al., J. Pept. Res. 52:121-9, 1998, and U.S. Pat. No. 5,444,150].

A particular method of cyclization involves stabilization of an amphipathic alpha-helix by using para-substituted amino acid derivatives of a benzene ring [Yu et al. (1999) id ibid]. Another particular method of cyclization is backbone cyclization, as disclosed in Reissmann et al., Biomed. Pept. Proteins Nucleic Acids 1:51-6, 1994-95, and in references therein. Another method of cyclization which involves backbone-to side chain connections may also be used [Reissmann et al. (1994-95) id ibid].

Nonetheless, according to the invention, the protein or polypeptide of the invention may be extended at the N-terminus and/or C-terminus thereof with various identical or different organic moieties which are not naturally occurring or synthetic amino acids. As an example for such extension, the protein or polypeptide may be extended at the N-terminus and/or C-terminus thereof with an N-acetyl group.

In order to improve polypeptide structure, the protein or polypeptide of the invention can be coupled through their N-terminus to a lauryl-cysteine (LC) residue and/or through their C-terminus to a cysteine (C) residue, or to other residue/s suitable for linking the polypeptide to adjuvant/s for immunization.

In another aspect, the present invention provides an isolated nucleic acid molecule comprising a sequence encoding the polypeptide denoted by any one of SEQ. ID. NO.1, SEQ. ID. NO.2, SEQ. ID. NO. 3 or SEQ. ID. NO. 4, and any fragments, derivatives, and analogs thereof, or the full length complement thereof.

Further, the present invention provides an isolated nucleic acid molecule that only differs in codon sequence from the nucleic acid molecule comprising a sequence encoding the polypeptide denoted by any one of SEQ. ID. NO.1, SEQ. ID. NO.2, SEQ. ID. NO. 3 or SEQ. ID. NO. 4, due to the degeneracy of the genetic code.

As used herein, the term "nucleic acid molecule" is intended to include DNA molecules (e.g., cDNA) and RNA molecules (e.g., mRNA) and analogs of the DNA or RNA generated using nucleotide analogs. The nucleic acid molecule can be single-stranded or double-stranded, but preferably it is double-stranded DNA.

The term "isolated nucleic acid molecule" is intended to include nucleic acid molecules which are separated from other nucleic acid molecules and which are substantially free of other cellular material, or culture medium when produced by recombinant techniques, or substantially free of chemical precursors or other chemicals when chemically synthesized.

Derivatives within the scope of the invention also include polynucleotide derivatives. Polynucleotide or nucleic acid derivatives differ from the sequences described or known in nucleotide sequence. For example, a polynucleotide derivative may be characterized by one or more nucleotide substitutions, insertions, or deletions.

One aspect of the invention pertains to nucleic acid fragments sufficient for use as hybridization probes to identify PRT5, PRT6, PRT7 or PRT8 protein-encoding nucleic acid molecules (e.g., PRT5-, PRT6-, PRT7- or PRT8-encoding mRNA) and fragments for use as PCR primers for the amplification or mutation of PRT5-, PRT6-, PRT7- or PRT8-encoding nucleic acid molecules.

In another embodiment, the isolated nucleic acid molecule comprising a sequence encoding the polypeptide denoted by SEQ. ID. NO.1, comprises the sequence denoted by SEQ. ID. NO. 5.

In a further embodiment, the isolated nucleic acid molecule comprising a sequence encoding the polypeptide denoted by SEQ. ID. NO.2, comprises the sequence denoted by SEQ ID. NO. 6.

In a further embodiment, the isolated nucleic acid molecule comprising a sequence encoding the polypeptide denoted by SEQ. ID. NO.3, comprises the sequence denoted by SEQ ID. NO. 7.

In a further embodiment, the isolated nucleic acid molecule comprising a sequence encoding the polypeptide denoted by SEQ. ID. NO.4, comprises the sequence denoted by SEQ ID. NO. 8.

A nucleic acid molecule of the present invention, e.g., a nucleic acid molecule having the nucleotide sequence of any one of any one of SEQ ID NO: 5, SEQ. ID. NO. 6, SEQ. ID. NO. 7 or SEQ. ID. NO. 8, or a portion thereof, can be generated using standard molecular biology techniques and the sequence information provided herein.

In a specific embodiment, an isolated nucleic acid molecule of the invention comprises the nucleotide sequence shown in any one of SEQ. ID. NO:5, SEQ. ID. NO. 6, SEQ. ID. NO. 7 or SEQ. ID. NO. 8.

In still another specific embodiment, an isolated nucleic acid molecule of the present invention comprises a nucleotide sequence which is at least about 80%, 85%, 90%, 95%, 98% or more homologous to the entire length of the nucleotide sequence shown in any one of SEQ. ID. NO. 5, SEQ. ID. NO. 6, SEQ. ID. NO. 7, and SEQ. ID. NO. 8.

Moreover, the nucleic acid molecule of the invention can comprise only a portion of the nucleic acid sequence of any one of SEQ. ID. NO. 5, SEQ. ID. NO. 6, SEQ. ID. NO. 7, and SEQ. ID. NO. 8, for example, a fragment which can be used as a primer, e.g., the sequence represented by any one of SEQ. ID. NO. 9, SEQ. ID. NO.10, SEQ. ID. NO.11, SEQ. ID. NO.12, SEQ. ID. NO. 13, SEQ. ID. NO. 14, SEQ. ID. NO. 15, or SEQ. ID. NO. 16, or a fragment encoding a portion of any one of the PRT5, PRT6, PRT7 or PRT8 protein, e.g. a biologically active portion of any one of the PRT5, PRT6, PRT7 or PRT8 protein. In a preferred embodiment, a nucleic acid molecule comprises at least 100 contiguous nucleotides of a nucleic acid comprising any one of SEQ. ID. NO. 5, SEQ. ID. NO. 6, SEQ. ID. NO. 7, or SEQ. ID. NO. 8.

Probes based on any one of the PRT5, PRT6, PRT7 or PRT8 nucleotide sequences can be used to detect transcripts encoding the same or homologous proteins. Such probes can be used as a part of a diagnostic test kit for identifying cells or tissue which express any one of PRT5, PRT6, PRT7 or PRT8 protein of the invention, such as by measuring a level of a PRT5-, PRT6-, PRT7- or PRT8-encoding nucleic acid in a sample of cells from a subject e.g., detecting PRT5, PRT6, PRT7 or PRT8 mRNA levels.

A nucleic acid fragment encoding a "biologically active portion" of any one of PRT5, PRT6, PRT7 or PRT8 protein can be prepared by isolating a portion of the nucleotide sequence of any one of SEQ. ID. NO. 5, SEQ. ID. NO. 6, SEQ. ID. NO. 7, and SEQ. ID. NO. 8, respectively, which encodes a polypeptide having PRT5, PRT6, PRT7 or PRT8 protein biological activity, expressing the encoded portion of the protein (e.g., by recombinant expression in vitro) and assessing the activity of the encoded portion of the protein. In a specific embodiment, a polynucleotide of the invention encodes a fragment comprising at least 30 contiguous amino acid residues of the amino acid sequence of any one of SEQ. ID. NO. 1, SEQ. ID. NO. 2, SEQ. ID. NO. 3, and SEQ. ID. NO. 4.

The invention further encompasses nucleic acid molecules that differ from the nucleotide sequence shown in any one of SEQ. ID. NO. 5, SEQ. ID. NO. 6, SEQ. ID. NO. 7, and SEQ. ID. NO. 8 due to degeneracy of the genetic code and thus encode the same PRT5, PRT6, PRT7 or PRT8 protein as those encoded by the nucleotide sequence shown in any one of SEQ. ID. NO. 5, SEQ. ID. NO. 6, SEQ. ID. NO. 7, and SEQ. ID. NO. 8, respectively.

In one embodiment, an isolated nucleic acid molecule of the invention has a nucleotide sequence encoding a protein having an amino acid sequence shown in any one of SEQ. ID. NO. 1, SEQ. ID. NO. 2, SEQ. ID. NO. 3, and SEQ. ID. NO. 4, or a fragment thereof. In another embodiment, an isolated nucleic acid molecule of the invention has a nucleotide sequence encoding a protein having at least about 80%, 85%, 90%, 95%, 98% or more identity to any one of SEQ. ID. NO. 1, SEQ. ID. NO. 2, SEQ. ID. NO. 3, and SEQ. ID. NO. 4, or a fragment thereof.

In addition to the PRT5, PRT6, PRT7 or PRT8 nucleotide sequences shown in SEQ. ID. NO. 5, SEQ. ID. NO. 6, SEQ. ID. NO. 7, and SEQ. ID. NO. 8, respectively, it will be appreciated by those skilled in the art that DNA sequence polymorphisms that lead to changes in the amino acid sequences of the polypeptide components of the PRT5, PRT6, PRT7 or PRT8 proteins may exist within a population. Such genetic polymorphism in the polypeptides of the PRT5, PRT6, PRT7 or PRT8 genes may exist within a population due to natural allelic variation.

Functional allelic variants will typically contain conservative substitution of one or more amino acids of any one of SEQ. ID. NO. 1, SEQ. ID. NO. 2, SEQ. ID. NO. 3, and SEQ. ID. NO. 4, or substitution, deletion or insertion of non-critical residues in non-critical regions of the protein.

Non-functional allelic variants will typically contain a non-conservative substitution, a deletion, or insertion, or premature truncation of the amino acid sequence of any one of SEQ. ID. NO. 1, SEQ. ID. NO. 2, SEQ. ID. NO. 3, and SEQ. ID. NO. 4, or a substitution, insertion, or deletion in critical residues or critical regions of the protein.

An isolated nucleic acid molecule encoding a PRT5, PRT6, PRT7 or PRT8 protein homologous to the protein of any one of SEQ. ID. NO. 1, SEQ. ID. NO. 2, SEQ. ID. NO. 3, and SEQ. ID. NO. 4, respectively, can be created by introducing one or more nucleotide substitutions, additions or deletions into the nucleotide sequence of SEQ. ID. NO. 5, SEQ. ID. NO. 6, SEQ. ID. NO. 7, and SEQ. ID. NO. 8, respectively, such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues.

Thus, a predicted nonessential amino acid residue in any one of PRT5, PRT6, PRT7 or PRT8 protein is preferably replaced with another amino acid residue from the same side chain family. Alternatively, in another embodiment, mutations can be introduced randomly along all or part of any one of PRT5, PRT6, PRT7 or PRT8 DNA coding sequence, such as by saturation mutagenesis, and the resultant mutants can be screened for PRT5, PRT6, PRT7 or PRT8 protein biological activity to identify mutants that retain PRT5, PRT6, PRT7 or PRT8 activity. Following mutagenesis of any one of SEQ. ID. NO. 5, SEQ. ID. NO. 6, SEQ. ID. NO. 7, and SEQ. ID. NO. 8, the encoded protein can be expressed recombinantly and the activity of the protein can be determined.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90% or 95% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In one embodiment, the percent identity between two amino acid sequences is determined using the Needleman and Wunsch (J. Mol. Biol. (48):444-453 (1970)) algorithm which has been incorporated into the GAP program in the GCG software package (available online through Accelrys Inc. website (formerly Genetics Computer Group), San Diego, Calif.), using either a Blossom 62 matrix or a PAM250 matrix, and a gap weight of 16, 14, 12, 10, 8, 6, or 4 and a length weight of 1, 2, 3, 4, 5, or 6. In another embodiment, the percent identity between two nucleotide sequences is determined using the GAP program in the GCG software package (available online through Accelrys Inc. website (formerly Genetics Computer Group), San Diego, Calif.), using a NWSgapdna.CMP matrix and a gap weight of 40, 50, 60, 70, or 80 and a length weight of 1, 2, 3, 4, 5, or 6. In yet another embodiment, the percent identity between two amino acid or nucleotide sequences is determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4.

Nucleic acid and protein sequences can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain homologous nucleotide sequences. BLAST protein searches can be performed with the) XBLAST program, score=50, wordlength=3 to obtain homologous amino acid sequences. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used. (See e.g., the National Center for Biotechnology Information on-line database).

Additionally, the "Clustal" method (Higgins and Sharp, Gene, 73:237-44, 1988) and "Megalign" program (Clewley and Arnold, Methods Mol. Biol, 70:119-29, 1997) can be used to align sequences and determine similarity, identity, or homology.

In yet another aspect the present invention provides a vector comprising an isolated nucleic acid molecule encoding the polypeptide as denoted by any one of SEQ. ID. NO. 1, SEQ. ID. NO. 2, SEQ. ID. NO. 3, and SEQ. ID. NO. 4, and any fragment, derivatives or analog thereof. Thus, said vector comprises an isolated nucleic acid sequence denoted by SEQ. ID. NO. 5, SEQ. ID. NO. 6, SEQ. ID. NO. 7, and SEQ. ID. NO. 8, respectively, or any variant thereof which only differs from it due to the degeneracy of the genetic code.

In one embodiment of said vector, said nucleic acid molecule is operably linked to a promoter.

In another embodiment, said vector is an expression vector.

As used herein, the term "vector" is intended to include a nucleic acid molecule capable of transporting another nucleic acid to which it has been linked. A vector may be characterized by one or a small number of restriction endonuclease sites at which such DNA sequences may be cut in a determinable fashion without the loss of an essential biological function of the vector, and into which a DNA fragment may be spliced in order to bring about its replication and cloning. A vector may further contain a marker suitable for use in the identification of cells transformed with the vector. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operatively linked" or "operably linked" is intended to mean that molecules are functionally coupled to each other in that the change of activity or state of one molecule is affected by the activity or state of the other molecule. Nucleotide sequences are "operably linked" when the regulatory sequence functionally relates to the DNA sequence encoding the polypeptide or protein of interest. For example, a promoter nucleotide sequence is operably linked to a DNA sequence encoding the protein or polypeptide of interest if the promoter nucleotide sequence controls the transcription of the DNA sequence encoding the protein of interest. Typically, two polypeptides that are operatively linked are covalently attached through peptide bonds.

In another further aspect the present invention provides a cell comprising the vector as described above, said vector comprising an isolated nucleic acid molecule encoding the polypeptide as denoted by any one of SEQ. ID. NO. 1, SEQ. ID. NO. 2, SEQ. ID. NO. 3, and SEQ. ID. NO. 4, and any fragment, derivatives or analog thereof, said vector comprising an isolated nucleic acid sequence denoted by SEQ. ID. NO. 5, SEQ. ID. NO. 6, SEQ. ID. NO. 7, and SEQ. ID. NO. 8, respectively, or any variant thereof which only differs from it due to the degeneracy of the genetic code.

In one embodiment, said cell is a host cell selected from the group consisting of: a plant cell, an insect cell, a fungal cell, a bacterial cell or a mammalian cell.

The terms "host cell" and "recombinant host cell" are used interchangeably herein. A "host cell" includes any cultivatable cell that can be modified by the introduction of heterologous DNA. Preferably, a host cell is one in which a transcriptional regulatory protein can be stably expressed, post-translationally modified, localized to the appropriate sub-cellular compartment, and made to engage the appropriate transcription machinery. The choice of an appropriate host cell will also be influenced by the choice of detection signal. For example, reporter constructs, as described above, can provide a selectable or screenable trait upon activation or inhibition of gene transcription in response to a transcriptional regulatory protein; in order to achieve optimal selection or screening, the host cell phenotype will be considered. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell of the present invention includes prokaryotic cells and eukaryotic cells. Prokaryotes include gram negative or gram positive organisms, for example, *E. coli* or Bacilli. Suitable prokaryotic host cells for transformation include, for example, *E. coli, Bacillus subtilis, Salmonella typhimurium*, and various other species within the genera *Pseudomonas, Streptomyces*, and *Staphylococcus*. Eukaryotic cells include, but are not limited to, yeast cells, plant cells, fungal cells, insect cells (e.g., baculovirus), mammalian cells, and the cells of parasitic organisms, e.g., trypanosomes.

As used herein, the term "yeast" includes not only yeasts in a strict taxonomic sense, i.e., unicellular organisms, but also yeast-like multicellular fungi of filamentous fungi. Exemplary species include *Kluyverei lactis, Schizosaccharomyces pombe*, and *Ustilaqo maydis*, with *Saccharomyces cerevisiae* being preferred. Other yeast which can be used in practicing the present invention are *Neurospora crassa, Aspergillus niger, Aspergillus nidulans, Pichia pastoris, Candida tropicalis*, and *Hansenula polymorpha*.

Mammalian host cell culture systems include established cell lines such as HeLa cells, COS cells, L cells, 3T3 cells, Chinese hamster ovary (CHO) cells, embryonic stem cells, etc.

In another further aspect, the present invention provides a composition comprising an isolated polypeptide or a protein selected from the group consisting of PRT5, PRT6, PRT7 and PRT8, wherein said protein or polypeptide comprises the sequence selected from the group consisting of SEQ. ID. NO. 1, SEQ. ID. NO. 2, SEQ. ID. NO. 3, or SEQ. ID. NO. 4, respectively, or any fragments, analogs of derivatives thereof, as defined above.

The inventors have surprisingly shown, in Examples 2 and 8 below (FIGS. 1A-1D and 5A-5B, respectively), that polypeptides PRT5 and PRT8 had a significant effect on glucose levels and glucose turnover. Both PRT5 and PRT8 induced a reduction in glucose levels measured post-glucose injection following starvation. These results were most prominent 2, 3 and 4 days following PRT5 injection, and 2 and 3 days following PRT8 injection.

These results suggest that PRT5 and PRT8 are regulators of glucose metabolism, and may be important therapeutic agents in the treatment of diabetes, or glucose metabolism-related disorders.

The results shown in Example 3 (FIGS. 2A-2B) further support the role of PRT5 as a regulator of glucose metabolism and as a factor in the diabetic condition. The reduced levels of PRT5 in diabetic patients strongly point to a significant role of PRT5 in diabetes. It may thus be inferred that PRT5, as well as PRT8, may be used as a therapeutic agent in the regulation of glucose metabolism, glucose turnover and even induction of insulin expression.

The inventors further surprisingly found that PRT5 is capable of increasing the levels of insulin receptors in skeletal muscle of mice treated with PRT5 (data not shown).

Insulin binds to its receptor which in turn starts many protein activation cascades. The insulin receptor (CD220) is a transmembrane receptor that is activated by insulin and belongs to the large class of tyrosine kinase receptors. It is composed by two alpha subunits and two beta subunits make up the insulin receptor. The beta subunits pass through the cellular membrane and are linked by disulfide bonds. The alpha and beta subunits are encoded by a single gene (INSR).

Upon binding of insulin to its receptor, a complex cascade of events is initiated, which includes: translocation of Glut-4 transporter to the plasma membrane and influx of glucose, glycogen synthesis, glycolysis and fatty acid synthesis. These processes occur particularly on the outer membrane of insulin-responsive tissues, including muscle cells and adipose tissue, and result in an increase in the uptake of glucose from blood into these tissues.

Thus, is may be inferred that by inducing insulin receptor expression, PRT5 induces said cascade of events as well. Therefore PRT5 directly or indirectly induces translocation of Glut-4 transporter to the plasma membrane and influx of glucose, glycogen synthesis, glycolysis and fatty acid synthesis.

Glycogen synthesis is also stimulated by the insulin receptor via IRS-1. In this case, it is the SH2 domain of PI-3 kinase (PI-3K) that binds the P-Tyr of IRS-1. Now activated, PI-3K can convert the membrane lipid phosphatidylinositol 4,5-bisphosphate (PIP2) to phosphatidylinositol 3,4,5-triphosphate (PIP3). This indirectly activates a protein kinase, PKB (Akt), via phosphorylation. PKB then phosphorylates several target proteins, including glycogen synthase kinase 3 (GSK-3). GSK-3 is responsible for phosphorylating (and thus deactivating) glycogen synthase. When GSK-3 is phosphorylated, it is deactivated, and prevented from deactivating glycogen synthase. In this roundabout manner, insulin increases glycogen synthesis.

Thus, in one specific aspect, the present invention provides a composition comprising any one of the isolated polypeptide PRT5 or PRT8, particularly PRT5, or a protein comprising thereof or a nucleic acid encoding the same, for inducing the expression of insulin receptor, for inducing the translocation of Glut-4 transporter to the plasma membrane and influx of glucose, for inducing glycogen synthesis, and/or for inducing glycolysis and fatty acid synthesis.

In another specific aspect, the present invention provides a composition comprising any one of the isolated polypeptide PRT5 or PRT8, or a protein comprising thereof or a nucleic acid encoding the same, for the treatment of glucose metabolism-related disorders.

Insulin resistance is a common and broadly prevalent metabolic disorder, which is intimately involved in the pathophysiology of diabetes, metabolic syndrome and obesity. It can also be a manifestation of various endocrine diseases, including polycystic ovary syndrome (PCOS), thyroid and adrenal diseases, as well as their complications.

The inventors unexpected results suggest that PRT5 could be used as a bypass mechanism for overcoming these disorders. Thus, PRT5 may be used as a therapeutic agent for the treatment of any pathologic condition related to insulin resistance, such as diabetes, metabolic syndrome, obesity and endocrine diseases, as well as muscle disorders.

Some of the most common diseases and disorders of the muscular system include myopathies, chronic fatigue syndrome, fibromyalgia, muscular dystrophy and compartment syndrome. Particular diseases related to defective skeletal muscle glucose and/or glycogen metabolism are myophosphorylase and phosphofructokinase deficiencies, more simply described by painful muscle cramps following exercise.

In another specific aspect, the present invention provides a composition comprising any one of the isolated polypeptide PRT5 or PRT8, or a protein comprising thereof or a nucleic acid encoding the same, for the treatment of a disorder selected from the group consisting of diabetes, metabolic syndrome, obesity, endocrine diseases, and muscle disorders.

In a further specific aspect the present invention provides a composition comprising any one of the isolated polypeptide PRT5 or PRT8, or a protein comprising thereof or a nucleic acid encoding the same, for enhancing glucose metabolism.

Further, in Example 5 below (and in FIGS. 3A-3B), the inventors have surprisingly shown that polypeptide PRT6 had a significant effect increasing testosterone levels. These results strongly suggest that PRT6 is a potent agent for the induction and/or enhancement of testosterone production, and therefore may be used in the therapy of testosterone deficiency-related disorders, or even in healthy conditions for the induction of testosterone production.

Testosterone is synthesized by an enzymatic sequence of steps from cholesterol within the 500 million Leydig cells located in the interstitial compartment of the testis between the seminiferous tubules, which constitutes approximately 5% of mature testis volume. In addition, some extragonadal biosynthesis of testosterone and dihydrotestosterone from circulating weak adrenal androgen precursor DHEA within specific tissues has been described, although the net contribution of adrenal androgens to circulating testosterone is small. Testicular testosterone secretion is principally governed by luteinizing hormone (LH) through its regulation of the rate-limiting conversion of cholesterol to pregnenolone within Leydig cell mitochondria by the cytochrome P-450 cholesterol side-chain cleavage enzyme complex located on the inner mitochondrial membrane.

Testosterone is used clinically at physiologic doses for androgen replacement therapy and, at typically higher doses, testosterone or synthetic androgens based on its structure is also used for pharmacologic androgen therapy. The principal goal of androgen replacement therapy is to restore a physiologic pattern of androgen exposure to all the body's tissues. Such treatment aims to replicate physiological circulating testosterone levels and the full spectrum (including pre-receptor androgen activation) of natural androgen effects on tissues. Pharmacologic androgen therapy exploits the anabolic or other effects of testosterone or synthetic androgens on muscle, bone, and other tissues as hormonal drugs that are judged on their efficacy, safety, and relative cost effectiveness like other therapeutic agents.

Physiologic effects of testosterone may be classified as pre-peripubertal effects, pubertal effects and adult effects. The pre-peripubertal effects are the first observable effects of rising androgen levels at the end of childhood, occurring in both boys and girls, and are generally distinguishable as adult-type body odor; increased oiliness of skin and hair; acne; appearance of pubic hair; axillary hair; growth spurt, accelerated bone maturation; and hair on upper lip and sideburns. Pubertal effects begin to occur when androgen has been higher than normal adult female levels for months or years. In males, these are usual late pubertal effects, and occur in women after prolonged periods of heightened levels of free testosterone in the blood. These effects may be observed as:

Enlargement of sebaceous glands, which may cause acne;
Phallic enlargement or clitoromegaly;
Increased libido and frequency of erection or clitoral engorgement;
Pubic hair extends to thighs and up toward umbilicus;
Facial hair (sideburns, beard, moustache);
Loss of scalp hair (Androgenetic alopecia);
Chest hair, periareolar hair, perianal hair;
Leg hair;
Axillary hair;
Subcutaneous fat in face decreases;
Increased muscle strength and mass;
Deepening of voice;
Growth of the Adam's apple;
Growth of spermatogenic tissue in testicles, male fertility;
Growth of jaw, brow, chin, nose, and remodeling of facial bone contours;
Shoulders become broader and rib cage expands;
Completion of bone maturation and termination of growth. This occurs indirectly via estradiol metabolites and hence more gradually in men than women.

Adult testosterone effects are more clearly demonstrable in males than in females, but are likely important to both sexes. Some of these effects may decline as testosterone levels decrease in the later decades of adult life. These effects are generally recognized as:

Libido and clitoral engorgement/penile erection frequency;
Regulates acute HPA (Hypothalamic-pituitary-adrenal axis) response under dominance challenge;
Mental and physical energy;
Maintenance of muscle trophism;

Maintaining normal testosterone levels in elderly men has been shown to improve many parameters which are thought to reduce cardiovascular disease, risk such as increased lean body mass, decreased visceral fat mass, decreased total cholesterol, and glycemic control. Under dominance challenge, testosterone may play a role in the regulation of the fight-or-flight response. Further, testosterone regulates the population of thromboxane A2 receptors on megakaryocytes and platelets and hence platelet aggregation in humans.

A list of symptoms of low testosterone levels, particular in aging men, includes:

Erectile dysfunction (problems with erections);
Loss of libido (low sex drive);
Mood disturbances, including depression, irritability and feeling tired;
Loss of muscle size and strength;
Osteoporosis (bone thinning);
Increased body fat;
Difficulty with concentration and memory loss; and
Sleep difficulties.

Thus, in another further specific aspect the present invention provides a composition comprising the isolated polypeptide PRT6, or a protein comprising thereof or a nucleic acid encoding the same, for enhancing testosterone production.

In another further specific aspect, a composition comprising the isolated polypeptide PRT6, or a protein comprising thereof or a nucleic acid encoding the same, for the treatment of testosterone deficiency or low testosterone-related disorders.

The inventors have further surprisingly shown that PRT7 is elevated in cancer. A non-limiting example of this phenomena is shown herein in Example 7, wherein high levels of PRT7 were found in samples of patients with lung or pancreatic cancer. Furthermore, the inventors observed that PRT7 was capable of inducing p53 (data not shown).

The cancer suppressor protein p53 is known to be stabilized and activated by diverse cellular stresses such as heat shock, hypoxia, osmotic shock, and DNA damage, leading to the inhibition of cell growth and apoptosis (Ko and Prives, Genes Dev. 10: 1054-1072, 1996; Levine, Cell 88: 323-331, 1997; Oren, Cancer Biol. 5: 221-227, 1994). It has been also known that apoptosis and cell cycle arrest are the major tumor suppressing functions of p53 (Levine, Cell 88: 323-331, 1997). Besides cancer, examples of apoptosis-associated disorders include arteriosclerosis, Alzheimer's disease, amyotrophic lateral sclerosis, graft-versus-host disease, autoimmune lymphocytosis syndrome, and viral infection.

The finding that PRT7 may induce p53 strongly suggests that PRT7 may be used in cancer therapy.

Thus, in another further specific aspect, the present invention provides a composition comprising the isolated polypeptide PRT7, or a protein comprising thereof or a nucleic acid encoding the same, for treating cancer, and/or for inducing p53 expression, and/or for inducing apoptosis.

In one embodiment, any composition provided in the present invention may further comprise a pharmaceutically acceptable carrier, excipient, or diluent.

The preparation of compositions is well known in the art and has been described in many articles and textbooks, see e.g., Remington's Pharmaceutical Sciences, Gennaro A. R. ed., Mack Publishing Co., Easton, Pa., 1990, and especially pp. 1521-1712 therein.

Compositions of the invention may further comprise at least one of pharmaceutically acceptable adjuvant, carrier, diluent or excipient.

By the term "pharmaceutically acceptable carrier" it is meant any one of inert, non-toxic materials, which do not react with the active ingredient. The carrier is selected at times based on the desired form of the formulation. The carrier may also at times have the effect of the improving the delivery or penetration of the active ingredient to the target tissue, for improving the stability of the drug, for slowing clearance rates, for imparting slow release properties, for reducing undesired side effects etc. The carrier may also be a substance that stabilizes the formulation (e.g. a preservative), for providing the formulation with an edible flavor, etc. The carriers may be any of those conventionally used and is limited only by chemico-physical considerations, such as solubility and lack of reactivity with the antibodies of the invention, and by the route of administration. The carrier may include additives, colorants, diluents, buffering agents, disintegrating agents, moistening agents, preservatives, flavoring agents, and pharmacologically compatible carriers. In addition, the carrier may be an adjuvant, which, by definition are substances affecting the action of the active ingredient in a predictable way. Typical examples of carriers include (a) liquid solutions, where an effective amount of the active substance is dissolved in diluents, such as water, saline, natural juices, alcohols, syrups, etc.; (b) capsules (e.g. the ordinary hard- or soft-shelled gelatin type containing, for example, surfactants, lubricants, and inert fillers), tablets, lozenges (wherein the active substance is in a flavor, such as sucrose and acacia or tragacanth or the active substance is in an inert base, such as gelatin and glycerin), and troches, each containing a predetermined amount of active agent as solids or granules; (c) powders; (d) suspensions in an appropriate liquid; (e) suitable emulsions; (f) liposome formulation; and others.

In another embodiment, compositions of the invention may also optionally further comprise additional active agents, such as, but not limited to antibiotics, cytokines, lymphokines, growth factors, hormones, anti-oxidants, vitamins, etc.

In another further aspect the present invention provides the use of a polypeptide or a protein selected from the group consisting of PRT5, PRT6, PRT7 and PRT8, as defined above, for the preparation of a medicament for the treatment of a disease or disorder, said disease or disorder being selected from the group consisting of diseases that have an immunological component or etiology, infectious diseases, acute and chronic inflammatory diseases, cancer, transplantation and autoimmune diseases, diseases linked to fertility and disorders of carbohydrate metabolism.

In one particular further aspect, the present invention provides the use of any one of the isolated polypeptide PRT5 or PRT8, or a protein comprising thereof or a nucleic acid encoding the same, in the preparation of a medicament for the treatment of glucose metabolism-related disorders.

More specifically, the present invention provides the use of any one of the isolated polypeptide PRT5 or PRT8, or a protein comprising thereof or a nucleic acid encoding the same, in the preparation of a medicament for the treatment of a disorder selected from the group consisting of diabetes, metabolic syndrome, obesity, endocrine diseases, and muscle disorders.

In another particular further aspect, the present invention provides the use of the isolated polypeptide PRT6, or a protein comprising thereof or a nucleic acid encoding the same, in the preparation of a medicament for the treatment of testosterone deficiency or testosterone deficiency-related disorders.

In another particular further aspect, the present invention provides the use of the isolated polypeptide PRT7, or a protein comprising thereof or a nucleic acid encoding the same, in the preparation of a medicament for the treatment of cancer.

In yet another further aspect the present invention provides a method of treatment of a disease or disorder in a subject in need, said method comprising administering a therapeutic effective amount of the polypeptide or the protein selected from the group consisting of PRT5, PRT6, PRT7 and PRT8, as defined above, or a composition comprising thereof, to said subject, said disease or disorder being selected from the group consisting of diseases that have an immunological component or etiology, infectious diseases, acute and chronic inflammatory diseases, cancer, transplantation and autoimmune diseases, diseases linked to fertility, disorders of carbohydrate metabolism, diabetes, metabolic syndrome, obesity, endocrine diseases, and muscle disorders.

In another particular further aspect, the present invention provides a method for the treatment of a disorder selected from the group consisting of a glucose metabolism-related disorder, diabetes, metabolic syndrome, obesity, endocrine diseases, and muscle disorders, said method comprising administering a therapeutic effective amount of the isolated polypeptide PRT5 or PRT8, or a protein comprising thereof or a nucleic acid encoding the same, or a composition comprising thereof, to a subject in need.

In another particular further aspect, the present invention provides a method for enhancing glucose metabolism, said method comprising administering a therapeutic effective amount of the isolated polypeptide PRT5 or PRT8, or a protein comprising thereof or a nucleic acid encoding the same, or a composition comprising thereof, to a subject in need.

In another further particular aspect the present invention provides a method for inducing insulin receptor expression, said method comprising administering a therapeutic effective amount of the isolated polypeptide PRT5 or PRT8, particularly PRT5, or a protein comprising thereof or a nucleic acid encoding the same, or a composition comprising thereof, to a subject in need.

Similarly, the present invention provides a method for inducing insulin receptor expression in a cell, said method comprising contacting cells with an effective amount of PRT5, or biologically active fragments or derivatives thereof, or a composition comprising thereof. Said method may be an in vitro or ex vivo method. Said cells will usually be muscle cells, adipose cells, their progenitors, or any cell wherein insulin receptor expression may be desired.

In another particular further aspect, the present invention provides a method for the treatment of a testosterone deficiency-related disorder, or for enhancing testosterone production, said method comprising administering a therapeutic effective amount of the isolated polypeptide PRT6, or a protein comprising thereof or a nucleic acid encoding the same, or a composition comprising thereof, to a subject in need.

In another further aspect, the present invention provides a method for the treatment of cancer, said method comprising administering therapeutically effective amount of the isolated polypeptide PRT7, or a protein comprising thereof or a nucleic acid encoding the same, or a composition comprising thereof, to a subject in need.

Further, the present invention provides a method for inducing any one of p53, apoptosis or cell death in a cell, said method comprising contacting cells with an effective amount of PRT7, or biologically active fragments or derivatives thereof, or a composition comprising thereof. Said method may be an in vitro or ex vivo method. Said cells may be any cells where it may be desirable to induce p53 or to induce apoptosis or cell death, such as cancerous cells.

As referred to herein, the term "effective amount" means an amount necessary to achieve a selected result, which at present, involves the amount of PRT5, PRT6, PRT7 or PRT8, or biologically active derivatives thereof, necessary for treating a disorder.

Said therapeutic effective amount, or dosing, is dependent on severity and responsiveness of the disease state to be treated, with the course of treatment lasting one hour to several hours, one day to several days, or until a cure is effected or a diminution of the disease state is achieved. Persons of ordinary skill can readily determine optimum dosages, dosing methodologies and repetition rates. Optimum dosages may vary depending on the relative potency of each polypeptide or protein of the invention, or compositions comprising thereof, and can generally be estimated based on EC50, found to be effective in in vitro as well as in in vivo animal models. Persons of ordinary skill in the art can easily estimate repetition rates for dosing based on measured residence times, concentrations, and adjustment to the employed polypeptide or protein.

The terms "treat, treating or treatment" as used herein mean ameliorating one or more clinical indicia of disease activity in a patient having a disease or disorder. "Treatment" refers to therapeutic treatment.

By "patient" or "subject in need" is meant any mammal for which treatment of a disorder or disease is desired in order to overcome said disorder or disease, particularly a human subject.

Usually, a "therapeutically effective amount" is also determined by the severity of the disease in conjunction with the preventive or therapeutic objectives, the route of administration and the patient's general condition (age, sex, weight and other considerations known to the attending physician).

Various methods of administration may be used for delivering the polypeptides PRT5, PRT6, PRT7, or PRT8 described in the invention to a subject in need. Said polypeptides, or compositions comprising thereof may be delivered via intravenous (i.v.), intramuscular (i.m.), intraperitoneal (i.p.), or topical injections, or through any other route found suitable by the man skilled in the art. In order to be effective therapeutically, the polypeptides or proteins of the invention should be prepared in a way that would enable their stability in the system following administration.

As used herein, the term "disorder" refers to a condition in which there is a disturbance of normal functioning. A "disease" is any abnormal condition of the body or mind that causes discomfort, dysfunction, or distress to the person affected or those in contact with the person. Sometimes the term is used broadly to include injuries, congenital malformations, disabilities, syndromes, symptoms, deviant behaviors, and atypical variations of structure and function, chronic or permanent health defects resulting from disease.

The terms "disease", "disorder", "condition" and "illness" are equally used herein.

In an even further aspect, the present invention provides an antibody which specifically recognizes a polypeptide selected from the group consisting of PRT5, PRT6, PRT7 and PRT8, or any fragments or derivatives thereof. Specifically, said PRT5, PRT6, PRT7 or PRT8 polypeptide is denoted by SEQ. ID. NO. 1, SEQ. ID. NO. 2, SEQ. ID. NO. 3, or SEQ. ID. NO. 4, respectively. Non-limiting examples of fragments recognized by the antibodies of the invention are the peptides used as antigens for generating said antibodies. Thus, in a specific example the anti-PRT5 antibody recognizes the peptide denoted by SEQ. ID. NO. 17, the anti-PRT6 antibody recognizes the peptide denoted by SEQ. ID. NO. 18, the anti-PRT7 antibody recognizes the peptide denoted by SEQ. ID. NO. 19, and the anti-PRT8 antibody recognizes the peptide denoted by SEQ. ID. NO. 20.

As defined herein, the antibodies of the invention are usually naturally derived, or naturally produced. Thus, the antibodies are polyclonal antibodies or monoclonal antibodies. Alternatively, the antibodies of the invention may be synthetically produced by e.g. chemical synthesis, or recombinantly produced through the isolation of the specific mRNA from the respective antibody-producing cell or cell line. Said specific mRNA shall then undergo standard molecular biology manipulations (obtaining cDNA, introducing said cDNA into expression vectors, etc.) in order to generate a recombinantly produced antibody. Said techniques are well known to the man skilled in the art.

As described in the Examples below, the antibodies of the present invention were generated in rabbit, using the standard techniques known to the man skilled in the art of generating polyclonal antibodies.

The generation of polyclonal antibodies against proteins is a technique well known to the man skilled in the art, and it is described, inter alia, in Chapter 2 of Current Protocols in Immunology, John E. Coligan et al. (eds.), Wiley and Sons Inc.

According to the invention, the polyclonal antibody recognizing anyone of the PRT5, PRT6, PRT7 or PRT8 antigen means that the principal recognition site of the polyclonal antibody corresponds to the PRT5, PRT6, PRT7 or PRT8 antigen, respectively. Generally, PRT5, PRT6, PRT7 or PRT8 or a fragment thereof is used as an immunogen for immunizing animals such as rabbit, guinea pig, goat, mouse, rat, sheep, monkey, for generating one of the antibodies described in the invention. From the resulting anti-PRT5, anti-PRT6, anti-PRT7 or anti-PRT8 antiserum, respectively, the antibody fraction is purified by a known method. The resulting antibody is used as the polyclonal antibody. As to the specificity of the polyclonal antibody, PRT5, PRT6, PRT7 or PRT8 is to be recognized, respectively. The principal recognition site of the polyclonal antibody resides in the C-terminal region of the PRT5, PRT6, PRT7 or PRT8 protein. The polyclonal antibody with the principal recognition site in the C-terminal region is an antibody recognizing, for example, the peptide denoted by SEQ ID NO.17, or the peptide denoted by SEQ ID NO.18, or the peptide denoted by SEQ ID NO.19, or the peptide denoted by SEQ ID NO.20, respectively.

Generally, polyclonal antibodies are prepared from immunoglobulin purified from animal sera immunized with immunogens. Polyclonal antibodies from different lots may also be mixed together so as to avoid the individual differences derived from individual animals and the lot difference in antisera. Because polyclonal antibodies are assemblies of antibodies, polyclonal antibodies have plural recognition sites.

Monoclonal antibodies may be prepared from B cells taken from the spleen or lymph nodes of immunized animals, in particular rats or mice, by fusion with immortalized B cells under conditions which favor the growth of hybrid cells. The technique of generating monoclonal antibodies is described in many articles and textbooks, such as the above-noted Chapter 2 of Current Protocols in Immunology. Spleen or lymph node cells of these animals may be used in the same way as spleen or lymph node cells of protein-immunized animals, for the generation of monoclonal antibodies as described in Chapter 2 therein. The techniques used in generating monoclonal antibodies are further described by Kohler and Milstein [Kohler and Milstein (1975) Nature 256; 495-497], and in U.S. Pat. No. 4,376,110.

The term "antibody" is also meant to include both intact molecules as well as fragments thereof, such as, for example, scFv, Fv, Fab', Fab, diabody, linear antibody, F(ab')$_2$ antigen binding fragment of an antibody which are capable of binding antigen [Wahl et al. (1983) J. Nucl. Med. 24, 316-325]. Fab and F(ab')$_2$ and other fragments of the antibodies are useful in the detection of the proteins used as antigens for the generation of the antibodies of the invention, in biological samples, according to the methods disclosed herein for intact antibody molecules, as well as for the other uses of the antibodies disclosed herein. Such fragments can be produced for example by proteolytic cleavage, using enzymes such as papain (to produce Fab fragments) or pepsin (to produce F(ab')$_2$ fragments). Thus, the Fab and F(ab')$_2$ and other fragments of the antibodies useful in the present invention may be tagged with various tags, according to the intended use. These tags may be detectable tags, to facilitate detection, or toxic tags, which would kill tumor cells, or "inducing" tags, which may induce other cells or substances to kill tumor cells.

An antibody is said to be "capable of binding", or "recognizing" a molecule if it is capable of specifically reacting with the molecule (the antigen) and thereby the antibody binds to said molecule. The term "epitope" is meant to refer to the portion of any molecule capable of being bound by an antibody, which can also be recognized by that antibody or the cells producing that antibody. Epitopes or "antigenic determinants" usually consist of chemically active surface groupings of molecules such as amino acids or sugar side chains, and have specific three-dimensional structural characteristics as well as specific charge characteristics.

An "antigen" is a molecule or a portion of a molecule capable of being recognized and bound by an antibody. An antigen may have one or more than one epitope. The specific reaction referred to above is meant to indicate that the antigen will react, in a highly selective and specific manner, with its corresponding antibody and not with the multitude of other antibodies which may be evoked by other antigens.

In the present invention, the peptides denoted by SEQ. ID. NO. 17, SEQ. ID. NO. 18, SEQ. ID. NO. 19 and SEQ. ID. NO. 20 were used as antigens to generate the polyclonal antibodies of the invention, and are thus recognized by the antibodies of the invention. Similarly, the full-length proteins described herein may also be referred to as antigens that are recognized by and capable of binding to the antibodies of the invention, each one according to its own specificity (i.e., PRT5 to anti-PRT5, PRT6 to anti-PRT6, PRT7 to anti-PRT7, PRT8 to anti-PRT8).

The antibodies provided by the present invention may be of any isotype, IgG, IgM, IgE, IgA or IgD.

With regard to the antibodies, "biological characteristics" or "biological activity" usually refers to the antibodies' ability to specifically recognize the epitope, and consequently bind to it. The epitope may be part of the full-length protein or may be embedded in a fragment of the protein or in a polypeptide.

In a further aspect, the present invention provides a composition comprising as active ingredient the antibody as described in the invention. Thus, said antibody comprised as the active agent of the composition of the invention is an antibody or a fragment thereof that recognizes and binds a polypeptide selected from the group consisting of PRT5, PRT6, PRT7 or PRT8, or any fragments, analogs or derivatives thereof.

Said composition may be for use in diagnostic and/or therapeutic methods.

Said antibody or said composition comprising thereof are useful for diagnosis of diseases or disorders which affect any one of PRT5, PRT6, PRT7 or PRT8 expression and/or function. Alternatively, said antibody or a composition comprising thereof may be used for the treatment of diseases or disorders which affect any one of PRT5, PRT6, PRT7 or PRT8 expression and/or function.

In another embodiment, said composition comprising the antibody as described in the invention may be used in the treatment of cancer.

In Example 7 below, the inventors have surprisingly shown elevated levels of circulating PRT7 in samples obtained from male patients with pancreatic or lung cancer. PRT7 may thus be used as a marker for detecting cancer, pancreatic or lung cancer being a specific non-limiting example. Therefore, anti-PRT7 specific antibodies may be used as a diagnostic tool for cancer.

Thus, in one particular embodiment, said composition comprises the antibody which recognizes the polypeptide PRT7, or fragments or derivatives thereof.

In a further embodiment, the composition comprising an antibody as described in the invention may be used in the prognosis of cancer, for example. A particularly need for prognosis exists in patients undergoing cancer treatment, in which it is essential to have indicators for treatment efficacy. Therefore, a composition comprising at least one antibody as described in the invention should be capable to determine the outcome of the treatment through the detection or the determination of the levels of any one of PRT5, PRT6, PRT7 or PRT8 protein.

Also provided in the present invention is the antibody-producing cell line, which produces an antibody according to the invention. Thus, the present invention provides the hybridoma cell line producing a monoclonal antibody against a protein selected from the group consisting of PRT5, PRT6, PRT7 and PRT8.

In one embodiment, the antibody-producing cells are clonally isolated and immortalized in order to produce the antibody-producing cell lines which are also the object of the present invention. Cell immortalization may be achieved as per the methods known to the man skilled in the art, and described, e.g., by Lanzavecchia et al., 2007 [Lanzavecchia A, Corti D, Sallusto F. (2007) Human monoclonal antibodies by immortalization of B cells. *Curr Opin Biotechnology;* 18(6):523-8].

In another further aspect, the present invention provides the use of an antibody as described in the invention, said antibody recognizing a protein selected from the group consisting of PRT5, PRT6, PRT7 and PRT8, in the preparation of a diagnostic composition. In particular, said composition is for the diagnosis of a disease or disorder, said disease or disorder being selected from the group consisting of diseases that have an immunological component or etiology, infectious diseases, acute and chronic inflammatory diseases, cancer, transplantation and autoimmune diseases, diseases linked to fertility and disorders of carbohydrate metabolism.

As referred to herein, an autoimmune disease includes inflammatory bowel disease (IBD), Crohn's disease, multiple sclerosis (MS), autoimmune uveitis, autoimmune uveoretinitis, autoimmune thyroiditis, Hashimoto's disease, insulitis, Sjogren's syndrome, spontaneous abortions, experimental autoimmune myocarditis, rheumatoid arthritis (RA), lupus (SLE), psoriasis and diabetes, particularly type I. Additional examples of autoimmune diseases include Acute necrotizing hemorrhagic leukoencephalitis, Addison's disease, Agammaglobulinemia, Allergic asthma, Allergic rhinitis, Alopecia greata, Amyloidosis, Ankylosing spondylitis, Anti-GBM/Anti-TBM nephritis, Antiphospholipid syndrome (APS), Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune thrombocytopenic purpura (ATP), Axonal and neuronal neuropathies, Bal's disease, Behnet's disease, Bullous pemphigoid, Cardiomyopathy, Castleman disease, Celiac sprue (nontropical), Chagas' disease, Chronic fatigue syndrome, Chronic inflammatory demyelinating polyneuropathy (CIDP), Churg-Strauss syndrome, Cicatricial pemphigoid/benign mucosal pemphigoid, Cogan's syndrome, Cold agglutinin disease, Congenital heart block, Coxsackie myocarditis, CREST disease, Essential mixed cryoglobulinemia, Demyelinating neuropathies, Dermatomyositis, Devic disease, Discoid lupus, Dressler's syndrome, Endometriosis, Eosinophilic fasciitis, Erythema nodosum, Experimental allergic encephalomyelitis, Evan's syndrome, Fibromyalgia, Fibrosing alveolitis, Giant cell arteritis (temporal arteritis), Goodpasture's syndrome, Graves' disease, Guillain-Barre syndrome, Hemolytic anemia, Henoch-Schonlein purpura, Herpes gestationis, Hypogammaglobulinemia, Idiopathic thrombocytopenic purpura (ITP), IgA nephropathy, Immunoregulatory lipoproteins, Inclusion body myositis, Insulin-dependent diabetes (type1), Interstitial cystitis, Juvenile arthritis, Juvenile diabetes, Kawasaki syndrome, Lambert-Eaton syndrome, Leukocytoclastic vasculitis, Lichen planus, Lichen sclerosus, Ligneous conjunctivitis, Linear IgA disease (LAD), Lyme disease, Meniere's disease, Microscopic polyangilitis, Mixed connective tissue disease (MCTD), Mooren's ulcer, Mucha-Habermann disease, Myasthenia gravis, Myositis, Narcolepsy, Neutropenia, Ocular cicatricial pemphigoid, Osteoarthritis, Palindromic rheumatism, Paraneoplastic cerebellar degeneration, Paroxysmal nocturnal hemoglobinuria (PNH), Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, and III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Psoriatic arthritis, Idiopathic pulmonary fibrosis, Pyoderma gangrenosum, Pure red cell aplasia, Raynaud's phenomenon, Reflex sympathetic dystrophy, Reiter's syndrome, Relapsing polychondritis, Restless legs syndrome, Rheumatic fever, Sarcoidosis, Schmidt syndrome, Scleritis, Scleroderma, Sperm and testicular autoimmunity, Stiff person syndrome, Subacute bacterial endocarditis (SBE), Sympathetic ophthalmia, Takayasu's arteritis, Temporal arteritis/Giant cell arteritis, Thrombocytopenic purpura (TTP), Autoimmune thyroid disease, Tolosa-Hunt syndrome, Transverse myelitis and necrotizing myelopathy, Ulcerative colitis, Undifferentiated connective tissue disease (UCTD), Vasculitis, Vesiculobullous dermatosis, Vitiligo and Wegener's granulomatosis.

In a further aspect, the present invention provides the use of an antibody as described in the invention, said antibody being able to specifically recognize a polypeptide selected from the group consisting of PRT5, PRT6, PRT7 and PRT8, or fragments or derivatives thereof, in the preparation of a therapeutic composition.

The anti-PRT5, anti-PRT6, anti-PRT7, and anti-PRT8 antibodies, or fragments thereof, provided in the present invention, may be used to quantitatively or qualitatively detect the proteins, or their fragments, used as antigens for the generation of the antibodies of the invention, in a sample. This can be accomplished by techniques giving a visually detectable signal, which may be any one of fluorescence (immunofluorescence), a chromogenic product of an enzymatic reaction, production of a precipitate, chemiluminescence or bioluminescence. Employing a fluorescently or color-labeled antibody coupled with light microscopy, flow cytometry, or fluorometric detection as described below. Other techniques and labels which may be used for detecting the antibody include, but are not limited to colloidal gold, radioactive tag, GFP (green fluorescence protein), and the like, avidin/streptavidin-biotin, magnetic beads, as well as physical systems, e.g. nanotechnological system, sensitive to the actual binding.

The antibodies, or fragments thereof, provided in the present invention may be employed in histology staining, as in immunohistochemistry, immunofluorescence or immuno-electron microscopy, as well as for in situ detection of the proteins. In situ detection may be accomplished by removing a histological specimen from a subject, and contacting the labeled antibody of the present invention with such a specimen. The antibody (or fragment) is contacted by applying or by overlaying the labeled antibody (or fragment) to a biological sample (said specimen). Through the use of such a procedure, it is possible to determine not only the presence of the antigen, but also its distribution on the examined tissue. Using the present invention, those of ordinary skill will readily perceive that any of a wide variety of histological methods, such as staining procedures can be modified in order to achieve such in situ detection.

One of the ways in which an antibody in accordance with the present invention can be labeled and directly detected is by linking the same to an enzyme and used in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholine-esterase. The detection can be accomplished by colorimetric methods which employ a chromogenic substrate for the enzyme. Detection may also be accomplished by visual comparison of the extent of enzymatic reaction of a substrate with similarly prepared standards (this procedure is suitable for both soluble color products and non-soluble color products, e.g. on nitrocellulose or plastic supports).

In the present invention, detecting the reaction of the antibody with the antigen can be further aided, in appropriate instances, by the use of a secondary antibody or other ligand which is reactive with the ligand or reacted antibody, either specifically with a different epitope, or non-specifically Enzyme immunoassays such as immunofluorescence assays (IFA), photometric assays, enzyme linked immunoabsorbent assays (ELISA), ELISPOT assay, and immunoblotting can be readily adapted to accomplish the detection of the specific antibodies.

Other detection systems which may also be used include those based on the use of protein A derived from *Staphylococcus aureus* Cowan strain I, protein G from group C *Streptococcus* sp. (strain 26RP66), or systems which employ the use of the biotin-avidin binding reaction.

Other methods of immunoenzymatic detection in which the antibodies of the invention may be employed are Western blot, and dot blot. The sample is separated by electrophoresis and transferred to a nitrocellulose membrane or other suitable support. The sample to be tested (e.g. culture supernatant, a tissue sample) is then brought into contact with the membrane and the presence of the immune complexes formed is detected by the method already described. In a variation on this method, purified antibodies are applied in lines or spots on a membrane and allowed to bind. The membrane is subsequently brought into contact with the sample before and after culture to be tested and the immune complexes formed are detected using the techniques described herein.

The presence of antibody-antigen complexes may also be detected by agglutination. The antibodies according to this invention, may be used to coat, for example, latex particles which form a uniform suspension. When mixed with a sample, e.g. serum containing specific antigens recognized by the antibodies, the latex particles are caused to agglutinate and the presence of large aggregates can be detected visually.

For a review of immunological and immunoassay procedures applicable to the measurement of antibodies by immunoassay techniques, see Basic and Clinical Immunology [D. Stites et al. (eds.) (1994) Basic and Clinical Immunology, $8^{th}$ ed.].

Detecting the reaction of the antibody with the antigen can be facilitated by the use of an antibody or ligand that is labeled with a detectable moiety by methods known in the art. Such a detectable moiety allows visual detection of a precipitate or a color change, visual detection by microscopy, or automated detection by spectrometry or radiometric measurement or the like. Examples of detectable moieties include fluorescein and rhodamine (for fluorescence microscopy), horseradish peroxidase and alkaline phosphatase (for either light microscopy or electron microscopy and biochemical detection and for biochemical detection by color change), and biotin-streptavidin (for light or electron microscopy). The detection methods and moieties used can be selected, for example, from the list above or other suitable examples by the standard criteria applied to such selections [Harlow and Lane (1988) Antibodies: A Laboratory Manual, Cold Spring Harbor Laboratory, Cold Spring Harbor, N.Y.].

Detection may be accomplished using any of a variety of other immunoassays. For example, by radioactive labeling the antibodies or antibody fragments, it is possible to detect antigens through the use of a radioimmunoassay (RIA). A good description of RIA may be found in Laboratory Techniques and Biochemistry in Molecular Biology, by Work, T. S. et al., North Holland Publishing Company, NY (1978) with particular reference to the chapter entitled "An Introduction to Radioimmune Assay and Related Techniques" by Chard, T., incorporated by reference herein. The radioactive isotope can be detected by such means as the use of a gamma/beta counter or a scintillation counter or by autoradiography.

It is also possible to label an antibody in accordance with the present invention with a fluorescent compound. When the fluorescently labeled antibody is exposed to light of the proper wavelength, its presence can be then detected due to fluorescence. Among the most commonly used fluorescent labeling compounds are fluorescein isothiocyanate, rhodamine, phycoerythrine, phycocyanin, allophycocyanin, o-phthaldehyde and fluorescamine.

The antibody can also be detectably labeled using fluorescence emitting metals such as $^{152}E$, or others of the lanthanide series. These metals can be attached to the antibody using such metal chelating groups as diethylenetriamine pentaacetic acid (ETPA).

The antibody can also be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An antibody molecule of the present invention may be adapted for utilization in an immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantification of the ternary complex formed between solid-phase antibody, antigen, and labeled antibody.

Antibodies of the invention may be radiolabeled in order to be used for imaging of a number of different cancers. Radioisotopes like $In^{111}$ and $Tc^{99}$ are used for labeling antibodies and visualization by imaging techniques. Radio-immunoscintigraphy (RIS) is a functional examination that allows for the in vivo imaging of tumors. This is accomplished using radiolabeled antibodies and standard gamma scintillation cameras. Each patient receives a total body survey. The body survey is performed as a full-length anterior and posterior total-body acquisition. In each case, selective planar images of areas of known or suspected disease (including oblique and lateral views) are obtained in order to increase the accuracy of lesion size and location.

The antibodies of the invention may also be used in multiplex immunoassays for high throughput screening of compounds that are involved in different basic physiological conditions and diseases in human and murine immune systems. Multiplex immunoassays are known to the man skilled in the art, and have been described, inter alia, by Anderson and Davison [Anderson and Davison (1999) Am. J. Pathol. 154: 1017-1022].

Thus, as mentioned above, the present invention is useful as a screening assay for the detection or indication of the presence of a tumor or cancer in a subject. The antibodies, or fragments thereof, when directly conjugated to a detectable marker as described herein, may be used in the detection of the antigen (or a fragment thereof) in vivo, indicating the presence of cancerous cells, and visualized with the help of imaging techniques, by injection into a subject to be diagnosed and detection by imaging.

Furthermore, the antibody provided by the invention may be conjugated to cytotoxic drugs, in order to be used, either per se or as part of a composition, in the treatment, for example, of cancer.

Hence, as mentioned above, the antibodies provided by the invention are suitable as a delivery system for toxic drugs in order to kill cancerous, or pre-cancerous cells.

In another further aspect the present invention provides a method for the treatment of a disease or disorder in a subject in need, said method comprising administering to said subject a therapeutic effective dosage of an antibody which recognizes a protein selected from the group consisting of PRT5, PRT6, PRT7 and PRT8, or fragments or derivatives thereof, or a composition comprising thereof, said disease or disorder being selected from the group consisting of diseases that have an immunological component or etiology, infectious diseases, acute and chronic inflammatory diseases, cancer, transplantation and autoimmune diseases, diseases linked to fertility, disorders of carbohydrate metabolism, diabetes, metabolic syndrome, obesity, endocrine diseases, and muscle disorders.

Further, the antibodies presented herein may be used as the active agent of the medicament, or it may be a delivery system for toxic or therapeutic drugs in order to achieve the cells to be treated.

One example of a cytotoxic drug is an anti-proliferative drug molecule, which may be covalently coupled directly or via a linker to any one of the antibodies of the invention, i.e. to anti-PRT5, anti-PRT6, anti-PRT7, or anti-PRT8, and wherein said antibody may optionally be specifically cleavable by a protease abundant in or secreted by e.g. cancer cells, thereby preferentially releasing the anti-proliferative drug within, near or at said cancer cells by the action of the protease.

Examples of anti-proliferative drugs are cyclophosphamide, chlorambucil, busulfan, Melphalan, Thiotepa, ifosfamide, Nitrogen mustard, methotrexate, 5-Fluorouracil cytosine arabinoside, 6-thioguanine, 6-mercaptopurine, doxorubicin, daunorubicin, idorubicin, dactinomycin, bleomycin, mitomycin, plicamycin, epipodophyllotoxins vincristin, vinblastin, vinclestin, Etoposide, Teniposide, carmustin, lomustin, semustin, streptozocin, adrenocorticoids, estrogens, antiestrogens, progestins, aromatase inhibitors, androgens, anti-androgens, dacarbazin, hexamethylmelamine, hydroxyurea, mitotane, procarbazide, cisplastin, carboplatin, Melphalan, Methotrexate, and Chlorambucil.

Alternatively, the anti-PRT5, anti-PRT6, anti-PRT7, or anti-PRT8 antibodies may carry a specific substance such as a metal ion (iron or zinc or other) into the tumor, and thus serve as a means or a carrier to deliver toxic substances (radioactive or cytotoxic chemical i.e. toxin like ricin or cytotoxic alkylating agent or cytotoxic prodrug, as mentioned before) to the tumor. The linkage of the antibody and the toxin or radioisotope can be chemical. Examples of direct linked toxins are doxorubicin, chlorambucil, ricin, pseudomonas exotoxin etc. A hybrid toxin can be generated with dual specificity, for the antigen and for the toxin. Such a bivalent molecule can serve to bind to the tumor and to deliver a cytotoxic drug to the tumor or to bind to and activate a cytotoxic lymphocyte such as binding to the $T_3$-$T_i$ receptor complex.

The present invention also provides a method that may be used in assessing prognosis of a cancer which has already been diagnosed. In particular, it is important to follow up pre-, during and post-treatment. Alternatively, said method is also appropriate for cancer screening, particularly when the sample to be tested is a blood sample, which is one of the most "patient-friendly" types of sample to be obtained from patients.

Thus, in another further aspect, the present invention provides a method for the diagnosis of a disease or disorder a subject, said disease or disorder being selected from the group consisting of diseases that have an immunological component or etiology, infectious diseases, acute and chronic inflammatory diseases, cancer, transplantation and autoimmune diseases, diseases linked to fertility, disorders of carbohydrate metabolism, diabetes, metabolic syndrome, obesity, endocrine diseases, and muscle disorders, said method comprising the steps of:
a. provided a sample from said subject;
b. contacting said sample with an antibody according to the invention, said antibody being selected from a group consisting of anti-PRT5, anti-PRT6, anti-PRT7 and anti-PRT8 antibody, or with a composition comprising thereof;
c. detecting the formation of a complex between said at least one antibody and its specific antigen, through detection means; whereby the detection of a complex indicates that said subject suffers from cancer.

Thus, the present invention, in a further aspect, also provides a method for the diagnosis of cancer in a sample, said method comprising detecting the presence of PRT7 polypeptide, or the protein comprising thereof in a sample from a subject; whereby a sample presenting PRT7 levels higher than control is indicative of the presence of cancer.

In one particular embodiment, said cancer is lung cancer or pancreatic cancer.

When referring herein to a subject, said subject may be a mammal, human or non-human. Non-human mammals include, but are not limited to, cows, horses, dogs, cats, mice, rats, guinea-pigs, etc. Usually the subject is a human, particularly a patient, or a healthy individual.

In one embodiment of the diagnostic method of the invention, said sample is a blood sample.

In another embodiment of the diagnostic method of the invention, said sample is a biopsy of said cancer.

Hence, the present invention also provides a method of monitoring the efficacy of cancer treatment. Monitoring the efficacy of treatment is essential for assessing prognosis of cancer treatment. Hence, the method of diagnostic presented herein may be effected in a subject before, during or after cancer treatment, and the analysis of the results obtained at each time point (the pattern of the relation between at least two antigen-antibody complexes) compared to the pattern of the same complexes in the normal population. The closest the pattern of the subject to that of the normal population, indicates a successful treatment.

Cancer treatment, as referred to herein, relates to any treatment for eradicating the disease, including radiotherapy, chemotherapy, etc.

As used herein to describe the present invention, "tumor", "cancer", "malignant proliferative disorder" and "malignancy" all relate equivalently to a hyperplasia of a tissue or organ. If the tissue is part of the lymphatic or immune systems, malignant cells may include non-solid tumors of circulating cells. Malignancies of other tissues or organs may produce solid tumors. In general, non-solid and solid tumors are, for example, carcinoma, melanoma, leukemia, and lymphoma.

Non-limiting examples of types of cancer and tumors include adrenocortical cancer; bladder cancer; colon cancer; colorectal cancer; rectal cancer; neuroectodermal and pineal cancer; childhood brain stem glioma; childhood cerebellar astrocytoma; childhood cerebral astrocytoma; childhood medulloblastoma; childhood visual pathway glioma; meningioma; mixed glioma; oligodendroglioma; astrocytoma; ependymoma; pituitary adenoma; acoustic neuroma; paravertebral malignant teratoma; breast cancer; male breast cancer; mammary gland neoplasia; ovarian cancer; carcinoid tumour; cervical cancer; uterus cancer; endometrial cancer; vaginal cancer; vulva cancer; gestational trophoblastic cancer; fallopian cancer; leukemia, such as myeloid leukemia, chronic myelogenous leukemia, acute myelogenous leukemia with maturation, acute promyelocytic leukemia, acute non-lymphocytic leukemia with increased basophiles, acute lymphatic leukemia; acute myeloid leukemia; acute monocytic leukemia, acute myelomonocytic leukemia with eosinophilia, lymphocytic leukemia such as, acute lymphoblastic leukemia, chronic lymphocytic leukemia; lymphoma (Hodgkin's disease and Non Hodgkin's disease); malignant lymphoma, cutaneous T-cell lymphoma; Burkitt's lymphoma; myeloproliferative diseases; benign meningioma; mixed tumors of salivary gland; tumors in lip and oral cavity; pharynx; larynx, paranasal sinuses; colonic adenomas; ductal carcinoma; carcinoma of the eyelid; carcinoma of the conjunctiva; carcinoma of the lacrimal gland; renal cell carcinoma; metastasic adenocarcinoma; adenocarcinomas, such as small cell lung cancer, kidney, uterus, prostate; squamous cell carcinoma; choriocarcinoma; neuroblastoma; retinoblastoma; sarcoma; rhabdomyosarcoma; soft tissue sarcomas; Kaposi's sarcoma; Ewing's sarcoma; osteosarcoma; extraskeletal myxoid chondrosarcoma; uterine sarcoma; sarcoma of the orbit; brain, spinal cord, vascular system; hemangiosarcoma; Wilm's tumour; Fanconi anemia; Langerhan's cells histiocytosis; malignant rhabdoid tumour of kidney; liver cancer; endocrine cancers; endometrial cancer; esophageal cancer; eye cancer; gastric cancer; gastrointestinal cancers; genitourinary cancers; glioma; gynecological cancers; head and neck cancer; hepatocellular cancer; hypopharynx cancer; islet cell cancer; kidney cancer; laryngeal cancer; lung cancer; skin cancer; non-melanoma skin cancer; melanoma; malignant melanoma; malignant melanoma of the conjunctiva; malignant melanoma of the uvea; mesothelioma;

myeloma, multiple; nasopharyngeal cancer; esophageal cancer; pancreas cancer; pituitary cancer; prostate cancer; stomach cancer; testicular cancer; thymus cancer; thyroid cancer; transitional cells cancer; trophoblastic cancer; testicular and ovarian dysgerminoma.

As defined herein "sample" refers to any sample obtained from a subject, generally a mammalian subject. Examples of biological samples include body fluids and tissue specimens. The source of the sample may be derived from such physiological media as blood, serum, plasma, breast milk, pus, cerebrospinal fluid, swabs, tissue scrapings, washings, urine, feces, rinse fluid obtained from wash of body cavities, phlegm, swabs taken from body regions (throat, vagina, ear, eye, skin, sores tissue, such as lymph nodes, or the like). Tissue specimens include biopsies of spleen, lymph nodes, and any lymphocyte-containing tissue.

The term "sample" in the present specification and claims is used herein in its broadest sense.

Typically swabs and samples that are a priori not liquid are contacted with a liquid medium which is then contacted with the detecting agent.

In one particular embodiment of the invention, said sample to be used in the method of the invention is any one of a body fluid or a culture-derived sample.

A culture-derived sample may be a cell extract, a medium sample, or a culture from a body fluid, e.g. a culture of a blood sample.

"Whole blood" means blood collected from an animal or human. Whole blood may be collected with heparin, EDTA, citrate or any other substance that prevents coagulation and clotting.

The biological sample may be treated with a solid phase support or carrier such as nitrocellulose, or other solid support or carrier which is capable of immobilizing cells, cell particles or soluble proteins. The support or carrier may then be washed with suitable buffers followed by treatment with a detectably labeled antibody in accordance with the present invention, as noted above. The solid phase support or carrier may then be washed with the buffer a second time to remove unbound antibody. The amount of bound antigen or label on said solid support or carrier may then be detected by conventional means.

By "solid phase support", "solid phase carrier", "solid support", "solid carrier", "support" or "carrier" is intended any support or carrier capable of binding antigen or antibodies. Well-known supports or carriers, include glass, polystyrene, polypropylene, polyethylene, dextran, nylon amylases, natural and modified celluloses, polyacrylamides, and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, cylindrical, as in the inside surface of a test tube, or the external surface of a rod. Different carriers may be used for different antigens within the same tube. Alternatively, the surface may be flat such as a sheet, test strip, etc. Specific supports or carriers include polystyrene beads. Those skilled in the art will know many other suitable carriers for binding antibody or antigen, or will be able to ascertain the same by use of routine experimentation.

Other steps such as washing, stirring, shaking, filtering and the like may be added to the assays as is customary or necessary for the particular situation.

As defined herein, "culture medium" means any medium than can be used to sustain a sample to practice the present invention, including but not limited to RPMI 1640 with or without fetal calf (bovine) serum, preferably supplemented with appropriate antibiotics and glutamine, and optionally other additives, such as anti-fungal agents, non-essential amino acids, DTT, sodium pyruvate, etc. Other culture media which may be used in practicing the present invention include, but are not limited to, Eagles, Dulbecco's, McCoy's, Media 199, Waymouth's media, and serum free medium with or without supplement. In another embodiment the stimulant is without media.

The present invention also provides a method of treatment of a disease or disorder in a subject in need thereof, said disease or disorder being selected from the group consisting of diseases that have an immunological component or etiology, infectious diseases, acute and chronic inflammatory diseases, cancer, transplantation and autoimmune diseases, diseases linked to fertility and disorders of carbohydrate metabolism, said method comprising administering to said subject a therapeutically effective dosage of a polypeptide or an antibody of the invention. In particular, said polypeptide or antibody when used for treatment is conjugated to a cytotoxic drug, or serves as a carrier for the delivery of toxic substances to the target cell or tissue. In this context, a target cell is a cell which is associated with said disease or disorder.

The present inventors have shown, in the Examples below, that PRT7 is elevated in certain types of cancer. In particular, the inventors demonstrated that PRT7 is significantly elevated in male patients with pancreatic or lung cancer.

The present invention thus provides a method for the diagnosis of cancer in a sample, said method comprising detecting the presence of a PRT7 polypeptide, or the protein comprising thereof in a sample from a subject; whereby a sample presenting PRT7 levels higher than control is indicative of the presence of cancer.

In another further aspect the present invention provides a diagnostic kit for the diagnosis and/or the monitoring treatment efficacy and/or for assessing the prognosis of a disease or disorder, said disease or disorder being selected from the group consisting of diseases that have an immunological component or etiology, infectious diseases, acute and chronic inflammatory diseases, cancer, transplantation and autoimmune diseases, diseases linked to fertility and disorders of carbohydrate metabolism, said kit comprising the following components:

a. an antibody as described herein in the invention or a composition comprising thereof; and
b. instructions for carrying out the detection of the presence of an antigen in a sample, wherein said antigen is specifically recognized by said antibody.

Said kit may further comprise at least one of the following components:

a. at least one means for collecting a sample to be tested;
b. at least one reagent necessary for detection of said recognition of said antigen by said antibody; and
c. at least one control sample.

One specific example of a kit provided by the present invention is a kit comprising an antibody which specifically recognizes the PRT7 polypeptide, fragments or derivatives thereof, or the protein comprising thereof, said kit being effective for the diagnosis of cancer The subject may be a mammal, human or non-human. Usually the subject is a human patient, or a healthy individual.

In one embodiment, any such kit is an antibody (or a recognizing agent) capture assay kit, as e.g. an ELISA kit, which comprises a solid support, at least one antibody as defined in the invention, and optionally secondary antibodies when appropriate. The kit may further optionally comprise any other necessary reagents such as detectable moieties, enzyme substrates and color reagents as described above. The antibody capture diagnostic kit is, alternatively, an immunoblot kit generally comprising the components and reagents described herein. The particular reagents and other components included in the diagnostic kits of the present invention can be selected from those available in the art in accord with the specific diagnostic method practiced in the kit. Such kits can be used to detect the antibody in biological samples, such as tissue or body fluid, particularly whole blood, PBMC or leucocytes before and/or after culture, obtained from a subject.

Where mentioned in the diagnostic method of the invention suitable means, said suitable means may be an immune affinity procedure, an enzymatic assay, or means for detecting a structural feature, amongst others.

Where said suitable means are an immune affinity procedure, said procedure is any one of enzyme-linked immunosorbent assay (ELISA), Western Blot, immuno-precipitation, FACS, or any other immunoaffinity procedure utilizing the antibodies as described in the present invention.

In one particular embodiment, detection is effected through capture ELISA.

Capture ELISA (also known as "sandwich" ELISA) is a sensitive assay to quantify picogram to microgram quantities of substances (such as hormones, cell signaling chemicals, infectious disease antigens and cytokines.). This type of ELISA is particularly sought after when the substance to be analyzed may be too dilute to bind to the polystyrene microtiter plate (such as a protein in a cell culture supernatant) or does not bind well to plastics (such as a small organic molecule). Optimal dilutions for the capture antibody, samples, controls, and detecting antibodies as well as incubation times are determined empirically and may require extensive titration. Ideally, one would use an enzyme-labeled detection antibody. However, if the detection antibody is unlabeled, the secondary antibody should not cross-react with either the coating antibody or the sample. The appropriate negative and positive controls should also be included.

The capture or coating antibody to be used should be diluted in carbonate-bicarbonate buffer or PBS. Capture antibodies are typically plated at 0.2 to 10 µg/ml. It is preferable to use affinity purified antibodies or at a minimum use an IgG fraction. Generally samples are diluted in PBS in the 10 ng-10 µg/well range (the more sensitive the assay, the less sample is required).

As used herein in the specification, the term "detectable moiety" refers to any atom, molecule or a portion thereof, the presence, absence or level of which may be monitored directly or indirectly. One example includes radioactive isotopes. Other examples include (i) enzymes which can catalyze color or light emitting (luminescence) reactions and (ii) fluorophores. The detection of the detectable moiety can be direct provided that the detectable moiety is itself detectable, such as, for example, in the case of fluorophores. Alternatively, the detection of the detectable moiety can be indirect. In the latter case, a second moiety which reacts with the detectable moiety, itself being directly detectable is preferably employed. The detectable moiety may be inherent to the antibody. For example, the constant region of an antibody can serve as an indirect detectable moiety to which a secondary antibody having a direct detectable moiety can specifically bind.

Thus, secondary antibodies are particular suitable means for the detection of the antibody in the method of the invention. This secondary antibody may be itself conjugated to a detectable moiety. One of the ways in which an antibody in accordance with the present invention can be detectably labeled is by linking the same to an enzyme. This enzyme, in turn, when later exposed to an appropriate substrate, will react with the substrate in such a manner as to produce a chemical moiety which can be detected, for example, by spectrophotometric, fluorometric or by visual means. Enzymes which can be used to detectably label the antibody include, but are not limited to, horseradish peroxidase, alkaline phosphatase, malate dehydrogenase, staphylococcal nuclease, delta-5-steroid isomerase, yeast alcohol dehydrogenase, alpha-glycerophosphate dehydrogenase, triose phosphate isomerase, asparaginase, glucose oxidase, beta-galactosidase, ribonuclease, urease, catalase, glucose-6-phosphate dehydrogenase, glucoamylase and acetylcholinesterase.

The detection can be accomplished by colorimetric methods, which employ a chromogenic substrate for the enzyme. Detection may also be accomplished by visual comparison of the extent of enzymatic reaction of a substrate in comparison with similarly prepared standards.

The solid support to which the first antibody is bound may be any water-insoluble, water-insuspensible, solid support. Examples of suitable solid support include large beads, e.g., of polystyrene, filter paper, test tubes, and microtiter plates. The first antibody may be bound to the solid support by covalent bonds or by adsorption. The advantage of the use of a solid support is that no centrifugation step is needed for the separation of solid and liquid phase.

The solid support mentioned above can include polymers, such as polystyrene, agarose, Sepharose, cellulose, glass beads and magnetizable particles of cellulose or other polymers. The solid-support can be in the form of large or small beads or particles, tubes, plates, or other forms.

As a solid support, use is preferably made of a test tube of a microtiter plate the inner walls of which are coated with a first antibody, e.g., the anti-PRT5, anti-PRT6, anti-PRT7, or anti-PRT8 antibodies, or any fragment or derivative thereof prepared by the inventors for the present invention.

Reference to "determining" as used by the diagnostic methods of the present invention, includes estimating, quantifying, calculating or otherwise deriving the amount of biomarker present in a specific sample. This may be achieved by measuring an end point indication that may be for example, the appearance of a detectable product, any detectable change in e.g. substrate levels or any change in the rate of the appearance of the product or the disappearance of the substrate, or measuring the amount of antibody bound to a biomarker as described by the invention.

In all of said test kits said means for collecting a sample to be tested can be a swab, a pipette, or similar collection means and said incubation means can be a liquid or semisolid culture medium placed in a plate, test tube, a glass or plastic surface, a well, or on a strip of absorbent paper, or similar means.

It should be appreciated that any version of the kit has been designed so as to also allow the test to be run on a scanner and the results fed into the computer in real time. This will ensure that the entire information can be mailed directly to all concerned and that it will be stored intact for any future reference.

In another embodiment of the kit, said sample is any one of a body fluid and a culture-derived sample.

The samples to be brought in contact with the antibodies of the invention may be arranged in an array.

The term "array" as used by the methods and kits of the invention refers to an "addressed" spatial arrangement of the recognition-agent, i.e., at least one of the antibodies of the invention. Each "address" of the array is a predetermined specific spatial region containing a recognition agent. For example, an array may be a plurality of vessels (test tubes), plates, micro-wells in a micro-plate each containing a different antibody. An array may also be any solid support holding in distinct regions (dots, lines, columns) different and known recognition agents, for example antibodies. The array preferably includes built-in appropriate controls, for example, regions without the sample, regions without the antibody, regions without either, namely with solvent and reagents alone and regions containing synthetic or isolated proteins or peptides recognized by the antibodies (positive control). Solid support used for the array of the invention will be described in more detail herein after, in connection with the kits provided by the invention.

A solid support suitable for use in the kits of the present invention is typically substantially insoluble in liquid phases. Solid supports of the current invention are not limited to a specific type of support. Rather, a large number of supports are available and are known to one of ordinary skill in the art. Thus, useful solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, filters, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as Sepharose, nylon, latex bead, magnetic bead, paramagnetic bead, superparamagnetic bead, starch and the like.

It should be further noted that any of the reagents included in any of the methods and kits of the invention may be provided as reagents embedded, linked, connected, attached placed or fused to any of the solid support materials described above.

It should be noted that any antibody used by the methods and kits of the invention may also be a polyclonal, monoclonal, recombinant, e.g., a chimeric, or single chain antibody (ScFv) derived from the antibodies of the invention. The present invention is defined by the claims, the contents of which are to be read as included within the disclosure of the specification.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, a "disease or disorder associated with hyperglycemia" refers to diseases or disorders in which an excessive amount of glucose circulates in the blood plasma. This is generally a glucose level higher than 11.1 mmol/l (200 mg/dl), but symptoms may not start to become noticeable until even higher values such as 15-20 mmol/l (~250-300 mg/dl). According to the American Diabetes Association guidelines, a subject with a consistent range between 100 and 126 is considered hyperglycemic, while above 126 mg/dl or 7 mmol/l is generally held to have diabetes. Chronic levels exceeding 7 mmol/l (125 mg/dl) can produce organ damage. Diseases or disorders associated with hyperglycemia include diabetes mellitus (type 1 and type 2), nephropathy, retinopathy, cardiovascular diseases (e.g. stroke, myocardial infarction), glands dysfunction (e.g. thyroid, adrenal, or pituitary), pancreas diseases, sepsis, intracranial diseases (e.g encephalitis, brain tumors, brain bleeds, meningitis). Prolonged, major surgeries can temporarily increase glucose levels. Recent results also suggest that in a non-fasted state, acute hyperglycemia increases plasma triglycerides (TG) by stimulating hepatic TG secretion, in a manner which is independent of either plasma insulin or free fatty acids levels.

As used herein, "glycated hemoglobin" (also referred to as hemoglobin A1c, HbA1c, A1C, Hb1c, or HbA1c) is a form of hemoglobin that is measured primarily to identify the average plasma glucose concentration over prolonged periods of time. It is formed in a non-enzymatic glycation pathway by hemoglobin's exposure to plasma glucose. Normal levels of glucose produce a normal amount of glycated hemoglobin. As the average amount of plasma glucose increases (hyperglycemia), the fraction of glycated hemoglobin increases in a predictable way. In diabetes mellitus, higher amounts of glycated hemoglobin have been associated with cardiovascular disease, nephropathy, and retinopathy.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the intended scope of the invention.

Unless defined otherwise, all technical and scientific terms used herein have the same meaning as commonly understood by one of ordinary skill in the art to which this invention is related.

EXAMPLES

General Methods of Molecular Biology

A number of methods of the molecular biology art are not detailed herein, as they are well known to the person of skill in the art. Such methods include PCR, expression of cDNAs, transfection of human cells, and the like. Textbooks describing such methods are, e.g., Sambrook et al. (1989) *Molecular Cloning, A Laboratory Manual*, Cold Spring Harbor Laboratory, ISBN: 0879693096; F. M. Ausubel (1988) *Current Protocols in Molecular Biology*, ISBN: 047150338X, John Wiley & Sons, Inc. Furthermore, a number of immunological techniques are not in each instance described herein in detail, like for example Western Blot, as they are well known to the person of skill in the art. See, e.g., Harlow and Lane (1988) *Antibodies: a laboratory manual*, Cold Spring Harbor Laboratory.

ELISA General Protocol

Enzyme-linked Immunosorbent Assays (ELISAs) combine the specificity of antibodies with the sensitivity of simple enzyme assays, by using antibodies or antigens coupled to an easily-assayed enzyme. ELISAs can provide a useful measurement of antigen or antibody concentration. An ELISA is a five-step procedure: 1) coat the microtiter plate wells with antigen diluted in PBS incubate ON 4C and wash; 2) block all unbound sites to prevent false positive results in BSA/FCS in PBS incubate 1 h and wash; 3) add antibody to the wells incubate 1 h and wash; 4) add anti-human IgG conjugated to an enzyme incubate 1 h and wash; 5) reaction of a substrate with the enzyme to produce a coloured product, thus indicating a positive reaction.

FACS Protocol
1. Harvest, wash the cells and adjust cell suspension to a concentration of 1-5×10$^6$ cells/ml in ice cold PBS, 10% FCS, 1% sodium azide.
2. Add 0.1-10 μg/ml of the primary labelled antibody. Dilutions, if necessary, should be made in 3% BSA/PBS
3. Incubate for at least 30 min at room temperature or 4° C.
4. Wash the cells 3× by centrifugation at 400 g for 5 minutes and ressuspend them in 500 μl to 1 ml of ice cold PBS, 10% FCS, 1% sodium azide.
5. Analyze the cells on the flow cytometer.

ELISA Procedure:
1. Calibration curve: Prepare serial dilutions of the protein in PBS (Biological industries, Catalog No. 02-023-5A) from 2000 pg/ml to 31 pg/ml.
2. Thaw samples quickly in 37° C. bath.
3. Sample loading: Load 70 μl duplicates of each blood sample (no dilution) and 70 μl triplicates of the standard samples in a Maxisorp 96-wells plate (NUNC, F96 Maxisorp, Catalog No. 442404). Incubate at 4° C. overnight with shaking.
4. Washing: remove liquid and wash the plate 4 times using a multi-pipette with 300 μl 0.05% TW-20 (Amresco, Catalog No. 0777-1L) in PBS.
5. Blocking: dilute 5% BSA (MP biomedicals, Catalog No. 160069) in PBS. Load 300 μl of the blocking buffer in each well. Incubate at room temperature for 1 hour with shaking.
6. Washing: Repeat step #4.
7. Detection: dilute the specific antibody (affinity purified) 1:250 in diluent (0.05% TW-20, 0.1% BSA in PBS). Load 1000 of detection antibody in each well. Incubate at room temperature for 2 hours with shaking.
8. Washing: Repeat step #4 above.
9. HRP conjugate: dilute goat anti-rabbit HRP conjugate antibody (Cell signaling, Catalog No. 7074) 1:200 in diluent. Load 1000 of HRP conjugate in each well. Incubate for 30 minutes at room temperature with shaking.
10. Washing: Repeat step #4 above, only with 5 washings instead of 4.
11. Development: Add 1000 TMB (3,3',5,5'-tetramethybenzidine, Horseradish peroxidase substrate, Millipore, Catalog No. ES001-500ML) to each well, wait for blue color development, then add 50 μl 2N $H_2SO_4$ (Frutarom, Catalog No. 5552540).
12. In a microplate reader, check the wells absorbance at 450 nm.

Preparation of Polyclonal Antibodies

The polyclonal antibodies were produced in rabbits using the standard protocol for the preparation of polyclonal antibodies.

A polyclonal antibody against PRT5 was generated in rabbit using as antigen a C-terminal fragment of PRT5, containing the last 14 amino acids of said polypeptide. This fragment is denoted herein as SEQ. ID. NO. 17.

A polyclonal antibody against PRT6 was generated in rabbit using as antigen a C-terminal fragment of PRT6, containing the last 14 amino acids of said polypeptide. This fragment is denoted herein as SEQ. ID. NO. 18.

A polyclonal antibody against PRT7 was generated in rabbit using as antigen a C-terminal fragment of PRT7, containing the last 14 amino acids of said polypeptide. This fragment is denoted herein as SEQ. ID. NO. 19.

A polyclonal antibody against PRT8 was generated in rabbit using as antigen a C-terminal fragment of PRT8, containing the last 14 amino acids of said polypeptide. This fragment is denoted herein as SEQ. ID. NO. 20.

A number of immunological techniques are not in each instance described herein in detail, as they are well known to the person of skill in the art, and these are described in detail in e.g., Harlow and Lane (1988) *Antibodies: a laboratory manual*, Cold Spring Harbour Laboratory.

Reverse Transcriptase PCR (RT-PCR)

RT-PCR analysis was performed in various tissues, in order to establish the pattern of expression of the novel proteins isolated. The PCR conditions applied were 95° C. for 2 minutes, followed by 40 cycles of: 95° C. for 45 seconds, 59° C. for 45 seconds and 72° C. for 5 minutes, with an end cycle of 72° C. for 5 minutes.

Sequences

All the sequences referred to in the present invention are presented in Table 1 below.

TABLE 1

Sequences provided in the present invention

| SEQ. ID. NO. | Description | Sequence |
| --- | --- | --- |
| SEQ. ID. NO. 1 | PRT5 amino acid sequence | MKPMERWWSR ALFTTCPVGP SGCAAGLLWP RNTDARSPLH SQTLWVCSWA ALAQKHRCTV TPAQPAP |
| SEQ. ID. NO. 2 | PRT6 amino acid sequence | MPPFSVGLVV VVNVVCLMLY ESTTILRLYG IILFMRDLKL EVEDAKITIA LALRNS |
| SEQ. ID. NO. 3 | PRT7 amino acid sequence | MGMIVPPSLA AAGGASTTPR LHALRLTSLL HQHLDLCLHP SPLPTPPSAP CLSGLVPPDS SLSVLDTLQV |
| SEQ. ID. NO. 4 | PRT8 amino acid sequence | MLVFLKLWPQ CLFFALTFFL RNCIYFKDFL SHLFGSFAWN FLLSSRSMDP TSCWTAPIWR SHRPLNSAPV SESPNYPLFT WSLKPETCPG LLVSLYPA |

TABLE 1-continued

Sequences provided in the present invention

| SEQ. ID. NO. | Description | Sequence |
|---|---|---|
| SEQ. ID. NO. 5 | PRT5 - coding sequence | atgaagccaa tggaaagatg gtggtcacga gccctcttca ccacctgtcc agtcggaccc tctgggtgtg cagctgggct gctctggccc agaaacacag atgcacggtc acccctgcac agccagaccc tctgggtgtg cagctgggct gctctggccc agaaacacag atgcacggtc acccctgcac agccagcccc atga |
| SEQ. ID. NO. 6 | PRT6 - coding sequence | atgcctccat tttcagtagg cttggttgtt gtagtcaatg tggtgtgttt gatgctatat gagtctacta ctattctaag actgtatggc attattcttt ttatgagaga tctcaaatta gaggttgagg atgcaaagat aactattgcc ttggccctga ggaattct |
| SEQ. ID. NO. 7 | PRT7 - coding sequence | atggggatga ttgttcctcc ttccttagct gctgcaggag gagcctccac aacacctagg ttgcatgcat tgaggttgac aagtctgcta catcaacact tggacttatg tctccatccg tctccccttc ctaccccacc atctgctcct tgcctctctg gccttgtgcc ccccgactca tcattgtctg tactggacac tctccaagta tag |
| SEQ. ID. NO. 8 | PRT8 - coding sequence | atgttggtgt tcttgaagct ttggcctcag tgcctttttct ttgctctcac attcttcctg agaaattgca tctactttaa agatttcctt tcccacctat tggatctttt tgcttggaac tttctcctaa gctccaggtc catggatcct acttcctgct ggactgctcc catctggaga tcccacaggc ccctcaactc agcccctgtt tctgaatccc ctaattatcc tctatttact tggtcactca agccagagac ttgccсctggc ctccttgtct cgctgtaccc cgcctga |
| SEQ. ID. NO. 9 | RT-PCR primer (PRT5) | gaagccaatg gaaagatggt ggtc |
| SEQ. ID. NO. 10 | RT-PCR primer (PRT5) | ggtgaccgtg catctgtgtt tct |
| SEQ. ID. NO. 11 | RT-PCR primer (PRT6) | ggcttggttg ttgtagtcaa tgtgg |
| SEQ. ID. NO. 12 | RT-PCR primer (PRT6) | attcctcagg gccaaggcaa tagt |
| SEQ. ID. NO. 13 | RT-PCR primer (PRT7) | ttgttcctcc ttccttagct gctg |
| SEQ. ID. NO. 14 | RT-PCR primer (PRT7) | tccagtacag acaatgatga gtcggg |
| SEQ. ID. NO. 15 | RT-PCR primer (PRT8) | ttcttgaagc tttggcctca gtgc |
| SEQ. ID. NO. 16 | RT-PCR primer (PRT8) | gtctctggct tgagtgacca agta |
| SEQ. ID. NO. 17 | PRT5 peptide (C-terminal) | QKHRCTVTPA QPAP |
| SEQ. ID. NO. 18 | PRT6 peptide (C-terminal) | EDAKITIALA LRNS |
| SEQ. ID. NO. 19 | PRT7 peptide (C-terminal) | PPDSSLSVLD TLQV |
| SEQ. ID. NO. 20 | PRT8 peptide (C-terminal) | PETCPGLLVS LYPA |
| SEQ ID NO: 21 | sbPRT8 | KPETCPGLLV SLYPA |

TABLE 1-continued

Sequences provided in the present invention

| SEQ. ID. NO. | Description | Sequence |
|---|---|---|
| SEQ ID NO: 22 | PRT8 N-ter | SHLFGSFAWN FLLSS |
| SEQ ID NO: 23 | PRT8 C-ter | LLVSLYPA |

Example 1

Characterization of PRT5

A novel cDNA was isolated from human cDNA libraries, and its protein product named PRT5.

The following primers were used for the RT-PCR analysis:

SEQ ID NO. 9: gaagccaatggaaagatggtggtc

SEQ ID NO. 10: ggtgaccgtgcatctgtgtttct

The product of the PCR was sequenced. The PCR products were analyzed on agarose gels and stained with Cyber Green (Invitrogene), and the intensity of the PCR product was evaluated using BioRad ChemiDoc analyzer. The results are presented in Table 2 below, and demonstrate a high degree of expression in pancreas and testis, and also identifiable expression in the spleen, ovary and small intestine.

TABLE 2

| cDNA library | Signal | G3PDH | (Signal/G3PDH) | minimal ratio |
|---|---|---|---|---|
| Pancreas* | 8384 | 3898 | 2.150847 | 3.845123 |
| Spleen | 35476 | 20116 | 1.76 | 1.35 |
| Testis* | 35710 | 15003 | 2.38 | 1.85 |
| Ovary | 24435 | 18072 | 1.288606 | 1 |
| Small intestine | 23247 | 15424 | 1.507 | 1.117 |

Example 2

Effect of PRT5 Administration on Glucose Levels of C57B1 Mice

High expression of PRT5 in the pancreas, as shown above, suggested that PRT5 might be involved in glucose metabolism. Thus, the goal of this experiment was to verify the effect of PRT5 administration on glucose levels and turnover.

Procedure:

7 week-old female C57B1 mice (purchased from Harlan Laboratories Ltd., Jerusalem, Israel) were injected with:

Saline—3 mice×4
1 µg/mice PRT5 —3 mice×4
5 µg/mice PRT5 —3 mice×4

The mice were divided into 4 groups. The first group was starved and checked for blood glucose levels (using an Accu-Chek® Performa device, Roche Diagnostics) one day after injection; the second group—two days after injection, the third group—three days after injection and the fourth group—four days after injection. Starvation was done overnight (the night before glucose injection), and the next day 2 mg/kg of glucose was injected to each mouse. A time course analysis of glucose levels was performed with glucose levels checked at t=0, 30, 90, 120, 150 and 240 minutes. The protocol for PRT5 administration and glucose measurement is presented in Table 3 below.

TABLE 3

Summary of the protocol for PRT5 administration and glucose measurement

| Day | Group 1 | 2 | 3 | 4 |
|---|---|---|---|---|
| 1 | PRT5/Saline injection Starvation | PRT5/Saline injection | PRT5/Saline injection | PRT5/Saline injection |
| 2 | Glucose injection and measure | Starvation | | |
| 3 | | Glucose injection and measure | Starvation | |
| 4 | | | Glucose injection and measure | Starvation |
| 5 | | | | Glucose injection and measure |

The results are presented in FIGS. 1A-1D. In all the mice, glucose levels peaked in the first 30 minutes following injection. However, surprising results were observed starting 2 days after PRT5 administration, where the glucose levels in the mice administered 1 µg/kg or 5 µg/kg were significantly lower than glucose levels in the mice administered saline. This effect repeated itself up until the last day when glucose levels were measured, day 5 of the experiment, 4 days after injection of PRT5.

The inventors have also observed that PRT5 is capable of increasing the levels of insulin receptors in skeletal muscle of mice treated with PRT5 (data not shown).

Example 3

PRT5 Levels in Healthy and Type II Diabetic Human Blood

The aim of this experiment was to compare the levels of PRT5 in healthy and Type-II diabetic individuals.

Samples:

20 human blood serum samples were obtained from Bioreclamation, Inc, from males and females aged 50-80 years old, as follows:

10 samples from healthy individuals (5 males/5 females)

10 samples from Type II diabetes patients (6 males/4 females)

Samples were kept under −80° C. Detailed information on the samples is shown in Tables 4a and 4b below. All samples were from Caucasian individuals.

TABLE 4a

Details on the samples assayed for PRT5 levels (healthy)

| Vial # | GENDER | AGE |
|---|---|---|
| 1 | MALE | 60 |
| 2 | MALE | 60 |
| 3 | MALE | 61 |
| 4 | MALE | 60 |
| 5 | MALE | 61 |
| 6 | FEMALE | 62 |
| 7 | FEMALE | 60 |
| 8 | FEMALE | 61 |
| 9 | FEMALE | 63 |
| 10 | FEMALE | 65 |

TABLE 4b

Details on the samples assayed for PRT5 levels (Diabetes type II)

| Vial # | GENDER | AGE | MEDICATIONS | DIAGNOSIS |
|---|---|---|---|---|
| D1 | Male | 61 | Amaryl, Novolog, Zocor, Niaspan, Lisinopril, Neurontin, ASA | Type 2 Diabetes, HTN, High Cholesterol, Degenerative Arthritis |
| D2 | Male | 57 | Actos, Zocor, Lisinopril, ASA, Humalog | Type 2 Diabetes, HTN, High Cholesterol |
| D3 | Female | 51 | ActosPlusMet, Zocor, Benicar, Metoprolol, Effexor | Type 2 Diabetes, HTN, High Cholesterol |
| D4 | Male | 59 | Novolog, Simcor, Glimepride, Lovasa, Prinzide, Advair | Type 2 Diabetes with Neuropathy, HTN, High Cholesterol, Bronchial Asthma |
| D5 | Female | 71 | Pravial, Lipitor, Metoprolol, Tricor, Diovan, Metformin | Abnormal Cardiac Stress Test, Type 2 Diabetes, High blood pressure |
| D6 | Male | 76 | Atenolol, Clonidine, Crestor, Allopurinol, CellCept, Prednisone, Neoral | Type 2 Diabetes, Neuropathy |
| D7 | Male | 65 | Metoprolol, Januvia, Amaryl, Ramipril, Glumetza | Type 2 Diabetes, Neuropathy, High Cholesterol, Hypertension |
| D8 | Female | 64 | Omeprazole, Neurontin, Metformin, Actos, Accupril, Zocor, Diltiazem | Type 2 Diabetes, Neuropathy, High Cholesterol, Hypertension |
| D9 | Male | 61 | Actos, Diovan, Metoprolol, Zocor | Type 2 Diabetes, HTN, High Cholesterol |
| D10 | Female | 63 | Methotrexate, Folic Acid, Plaquenil, Glucophage, Prednisone, Diazide, Diovan | Rheumatoid Arthritis, HTN, Type 2 Diabetes |

PRT5 levels were detected through ELISA, using an anti-PRT5 antibody. ELISA procedure was a described above. Blood samples were not diluted and the anti-PRT5 antibody was diluted 1:250 in diluent (0.05% Tween20, 0.1% BSA in PBS). For the calibration curve, serial dilutions of PRT5 were prepared in PBS, from 4000 pg/ml to 62.5 pg/ml.

The results are shown in FIGS. 2A-2B. As shown particularly in FIG. 2B, the levels of PRT5 are significantly reduced in Type II diabetes samples.

The results shown here, together with the results described in Example 2 above, strongly suggest that PRT5 is intimately involved in glucose metabolism, and particularly in its regulation. Most importantly, both sets of results support the use of PRT5 as a therapeutic agent for the treatment of diabetes.

Example 4

Characterization of PRT6

A second novel cDNA was isolated from human cDNA libraries, and its protein product named PRT6.

The following primers were used for the RT-PCR analysis:

SEQ. ID. NO. 11: ggcttggttgttgtagtcaatgtgg

SEQ. ID. NO. 12: attcctcagggccaaggcaatagt

As in Example 1 above, tissue expression analysis was performed using RT-PCR, and the results obtained summarized in Table 5 below. Essentially, expression of PRT6 was found exclusively in the testis.

TABLE 5

Expression of PRT6

| cDNA library | Signal | G3PDH | (Signal/G3PDH) | minimal ratio |
|---|---|---|---|---|
| Testis* | 5710 | 19003 | 0.300479 | 1.430852 |

Example 5

Effect of PRT6 Administration on Male Balb/C Testosterone Level

High expression of PRT6 in the testis, as shown in Table 5, suggested that PRT6 might be involved in testosterone expression. Thus, the goal of this experiment was to verify the effect of PRT6 administration on testosterone levels.

Procedure:

Two groups of Balb/C mice were used:

3-4 week-old male Balb/C—Negative control for testosterone—18 mice 7-8 week-old male Balb/C mice—18 mice Each group was divided into 3 sub-groups (6 mice each). Each group was injected every day for a 4 day-period with 200 μl of one of the following:

4% DMSO in double-distilled water (DDW)

0.5 μg/kg of PRT6 (diluted in DDW)

5 μg/kg of PRT6 (diluted in DDW)

After 4 days, blood serum was extracted from the mice and tested for testosterone levels. Testosterone measurement was done using the R&D Systems Testosterone Immunoassay (R&D Systems Catalog Number KGE010). This assay is based on the competitive binding technique. A monoclonal antibody specific for testosterone binds to the goat anti-mouse antibody coated onto the microplate. Following a wash to remove excess monoclonal antibody, testosterone present in the sample competes with a fixed amount of horseradish peroxidase (HRP)-labeled testosterone for sites on the monoclonal antibody. This is followed by another wash to remove excess conjugate and unbound sample. A substrate solution is added to the wells to determine the bound enzyme activity. Color development is stopped, and absorbance is read at 450 nm. The intensity of the color is inversely proportional to the concentration of testosterone in the sample.

The results are presented in FIGS. 3A-3B. Interestingly, the mice treated with PRT6 displayed a significant increase in testosterone levels. The effects of the 5 μg/kg administration were much more pronounced than those following 0.5 μg/kg administration, although both treatments resulted in an increase of testosterone levels.

Example 6

Characterization of PRT7

A third novel cDNA was isolated from human cDNA libraries, and its protein product named PRT7.

The following primers were used for the RT-PCR analysis:

```
SEQ. ID. NO. 13: ttgttcctccttccttagctgctg

SEQ. ID. NO. 14: tccagtacagacaatgatgagtcggg
```

As in Example 1 above, tissue expression analysis was performed using RT-PCR, and the results obtained summarized in Table 6 below. Essentially, pronounced expression of PRT7 was found in fetal brain, and also in skeletal muscle and liver.

TABLE 6

Expression of PRT7

| cDNA library | Signal | G3PDH | (Signal/G3PDH) | minimal ratio |
|---|---|---|---|---|
| Brain | 3340 | 5971 | 0.55937 | 1.00000 |
| Liver | 7809 | 6002 | 1.3 | 2.32 |
| Skeletal muscle | 10849 | 6273 | 1.72 | 3.074 |
| Fetal brain | 8272 | 4069 | 2.032932 | 3.62 |

Example 7

PRT7 Levels in Human Blood of Healthy Individuals and of Pancreatic or Lung Cancer Patients This experiment aimed at verifying the levels of PRT7 in blood from healthy individuals, as well as from pancreatic or lung cancer patients.

Samples:

Pancreatic Cancer (I):

19 human blood serum samples were obtained from Bioreclamation, Inc. as follows:

Healthy: 5 males/4 females

Pancreatic cancer: 5 males/5 females

Pancreatic Cancer (II):

10 male human blood serum samples were obtained from Bioreclamation, Inc. as follows:

5 healthy 5 pancreatic cancer

Lung Cancer:

20 human (males and females) blood serum samples were obtained from Bioreclamation, Inc. from males and females:

10 healthy (5 males/5 females)

10 lung cancer (5 males/5 females)

Samples were kept under −80° C. Detailed information on the samples is shown in Tables 7a-7b, 8a-8b, and 9a-9b below. All samples were from Caucasian individuals.

TABLE 7a

Details on pancreatic cancer (I) samples (healthy - used as control)

| Vial # | GENDER | AGE |
|---|---|---|
| 1 | MALE | 60 |
| 2 | MALE | 60 |
| 3 | MALE | 61 |
| 4 | MALE | 60 |
| 5 | MALE | 61 |
| 6 | FEMALE | 62 |
| 7 | FEMALE | 60 |
| 8 | FEMALE | 61 |
| 9 | FEMALE | 63 |
| 10 | FEMALE | 65 |

TABLE 7b

Details on pancreatic cancer (I) samples (patients - male + female)

| Vial # | GENDER | AGE | MEDICATIONS | STAGE |
|---|---|---|---|---|
| C1 | MALE | 69 | Gemzar RT | 2 |
| C2 | MALE | 71 | Gemzar | 4 |
| C3 | MALE | 69 | None | 2 |
| C4 | FEMALE | 64 | Gemzar | 2 |

TABLE 7b-continued

Details on pancreatic cancer (I) samples (patients - male + female)

| Vial # | GENDER | AGE | MEDICATIONS | STAGE |
|---|---|---|---|---|
| C5 | FEMALE | 64 | Gemzar | 2 |
| C6 | FEMALE | 63 | Gemzar | 3 |
| C7 | FEMALE | 80 | Gemzar | 4 |
| C8 | FEMALE | 75 | Gemzar | 3 |
| C9 | MALE | 71 | Xeloda, Gemzar | 3 |
| C10 | MALE | 80 | None | 4 |

TABLE 8a

Details on pancreatic cancer (II) samples (all males) (healthy - used as control)

| Vial # | AGE |
|---|---|
| 1 | 62 |
| 2 | 63 |
| 3 | 48 |
| 4 | 47 |
| 5 | 54 |

TABLE 8b

Details on pancreatic cancer (II) samples (patients - all males)

| Vial # | AGE | MEDICATIONS | STAGE |
|---|---|---|---|
| C1 | 46 | Gemzar, Taxol | 4 |
| C2 | 69 | Gemzar | 2 |
| C3 | 57 | None | 2 |
| C4 | 61 | Gemzar | 2 |
| C5 | 58 | Gemzar | 2 |

TABLE 9a

Details on lung cancer samples (healthy - used as control)

| Vial # | GENDER | AGE |
|---|---|---|
| 1 | MALE | 60 |
| 2 | MALE | 60 |
| 3 | MALE | 61 |
| 4 | MALE | 60 |
| 5 | MALE | 61 |
| 6 | FEMALE | 62 |
| 7 | FEMALE | 60 |
| 8 | FEMALE | 61 |
| 9 | FEMALE | 63 |
| 10 | FEMALE | 65 |

TABLE 9b

Details on lung cancer samples (patients, male + female)

| Vial # | GENDER | AGE | MEDICATIONS | Stage |
|---|---|---|---|---|
| L1 | Female | 68 | Ibuprofen, Vicodin, Spiriva | |
| L3 | Female | 63 | Omeprazole, Nasonex, Levoxyl, Actonel, Calcium | |
| L4 | Female | 65 | Ambien, Hycodan syrup, Synthroid | 4 |
| L5 | Male | 70 | Taxol, Carboplatin | 4 |
| L6 | Female | 65 | Taxol, Carboplatin | 3 |
| L7 | Male | 68 | Cisplatin, Gemzar | 2 |
| L8 | Male | 53 | Cisplatin, Gemzar | 1 |
| L9 | Male | 69 | Cisplatin, Gemzar | 2 |
| L10 | Male | 63 | Cisplatin, Gemzar | 3 |

PRT7 levels were detected through ELISA, using an anti-PRT7 antibody. ELISA procedure was a described above. Blood samples were diluted 1:3 in PBS, and the anti-PRT7 antibody was diluted 1:200 in diluent (0.05% Tween20, 0.1% BSA in PBS). For the calibration curve, serial dilutions of PRT7 were prepared in PBS, from 4000 pg/ml to 62.5 pg/ml.

The results are shown in FIGS. 4A-4F. Surprisingly, PRT7 levels were significantly higher in samples from male pancreatic cancer patients (FIGS. 4B-4D), but not from female (FIGS. 4A-4B). Similarly, PRT7 levels were also significantly elevated in samples from male lung cancer patients, but not from female (FIGS. 4E-4F).

These results show that PRT7 may be a marker for both pancreatic and lung cancer in males, and therefore may be used as a diagnostic tool for the detection of pancreas and lung cancer in males.

Most surprisingly, the inventors further observed that PRT7 can induce the expression of p53 [data not shown].

Example 8

Characterization of PRT8

A fourth novel cDNA was isolated from human cDNA libraries, and its protein product named PRT8.

The following primers were used for the RT-PCR analysis:

```
SEQ. ID. NO. 15: ttcttgaagctttggcctcagtgc

SEQ. ID. NO. 16: gtctctggcttgagtgaccaagta
```

As in Example 1 above, tissue expression analysis was performed using RT-PCR, and the results obtained summarized in Table 10 below. Essentially, expression of PRT8 was found in testis, liver and pancreas.

TABLE 10

Expression of PRT8

| cDNA library | Signal | G3PDH | (Signal/G3PDH) | minimal ratio |
|---|---|---|---|---|
| Testis* | 7710 | 16003 | 0.48 | 0.48 |
| Liver | 4809 | 6702 | 0.71 | 1.0 |
| Pancreas* | 3384 | 3998 | 0.84 | 1.18 |

Example 9

Effect of PRT8 Administration on Glucose Levels of C57B1 Mice

Expression of PRT8 in the pancreas suggested that PT8 may be involved in pancreatic function, and particularly in glucose metabolism. Thus, the effect of PRT8 administration on glucose levels was examined.

Procedure:

7 week-old female C57B1 mice (purchased from Harlan Laboratories Ltd., Jerusalem, Israel) were injected with:
  Saline—3 mice×2 groups
  1 µg/mouse PRT8 —3 mice×2 groups
  10 µg/mouse PRT8 —3 mice×2 groups All the mice were injected with PRT8 (or saline) on day 1. The first group was starved on day 2 and checked for blood glucose levels (using an Accu-Chek®Performa device, Roche Diagnostics) on day three. The second group was starved and checked for blood glucose levels three days after injection. Starvation was done overnight (the night before glucose injection), and the next day 2 mg/kg of glucose was injected to each mouse. A time course analysis of glucose levels was performed with glucose levels checked at t=0, 30, 60 and 120 minutes following glucose injection.

The results are presented in FIGS. 5A-5B. In all the treatments, glucose levels peaked in the first 30 minutes following injection. However, surprising results were observed starting 2 days after PRT8 administration, where the glucose levels in the mice administered 1 µg/kg or 10 µg/kg of PRT8 were significantly lower than glucose levels in the mice administered saline. This effect was more evident when analysis of glucose levels was done three days following PRT8 injection. These results strongly suggest that PRT8 is intimately involved in glucose metabolism and can be used in its regulation.

Example 10

Effect of sbPRT8 Administration on Glucose Levels of C57B1/6 Mice Treated with Streptozotocyn (STZ)

In the following experiments, a sbPRT8 peptide blocked with an acetyl moiety at the N-terminal end and an amide moiety ($NH_2$) at the C-terminal end has been employed. The effect of sbPRT8 administration on glucose levels was examined and compared to the effect obtained with PRT8 in mice treated with streptozocin (STZ). As known in the art, STZ is a chemical compound that is particularly toxic to the insulin-producing beta cells of the pancreas in mammals. It is used in medicine for treating certain cancers of the Islets of Langerhans and used in medical research to produce an animal model for Type 1 diabetes as well as Type 2 diabetes.

Experience 1:

C57B1/6 males mice were purchased from Harlan Laboratories Ltd., Jerusalem, Israel, After 7 days of rest, mice were IP injected with 50 mg/kg STZ for 4 days. Five days after STZ injection, mice were treated as follows:

Group A (control)—100 µg/mice of PRT8 (control)
  Group B (treatment)—20 µg/mice of sbPRT8 (treatment 1)
  Group C (control)—100 µg/mice of sbPRT8 (treatment 2)

After 5 weeks of treatment mice were starved for food only for 12 h and then were IP injected with 1 mg/kg of glucose solution (IPGTT). The level of glucose in mice blood was measured with Accucheck glucometer (Roche) at t=0, 15, 30, 60, 90 and 120 minutes following glucose injection.

Experience 2:

C57B1/6 males mice were purchased from Harlan Laboratories Ltd., Jerusalem, Israel. After 7 days of rest, mice were IP injected with 50 mg/kg STZ for 4 days. Five days after STZ injection, mice were treated as follows:

Group A (control)—100 µg/mice of PRT8 (control)
  Group B (treatment)—100 µg/mice of sbPRT8 (treatment 1)
  Group C (control)—300 µg/mice of sbPRT8 (treatment 2)

After 4 weeks of treatment mice were starved for food only for 12 h and then were IP injected with 1 mg/kg of glucose solution (IPGTT). The level of glucose in mice blood was measured with Accucheck glucometer (Roche) at t=0, 15, 30, 60, 90 and 120 minutes following glucose injection.

The results are shown in FIGS. 6A-6B. In all the treatments, glucose levels peaked in the first 30 minutes following injection. While injection of PRT8 enables a significant reduction of blood glucose level in mice (see also Example 9), the injection of sbPRT8 shows a surprising and very significant improvement in said reduction of blood glucose level. These results clearly demonstrate that the peptide of SEQ ID NO: 21 (sbPRT8), which is a C-terminal fragment of PRT8, has an improved glucose reduction activity over the full length PRT8 peptide. Similar experiments were conducted with two other PRT8 fragments of SEQ ID NO: 22 (PRT8 N-ter) and SEQ ID NO: 23 (PRT8 C-ter), and contrary to the results obtained with sbPRT8, no significant blood glucose reduction was observed.

From the aforesaid, it can be concluded that the short peptide sbPRT8 shows a significantly improved potential in glucose metabolism regulation and blood glucose level reduction over the full length PRT8 peptide. sbPRT8 may be thus of great interest for treating diseases or disorders associated with hyperglycemia. Furthermore, sbPRT8 may be used to decrease the blood level of glycated hemoglobin (HbA1c level) and lower the plasma triglycerides (TG) level, since both levels are closely related to blood glucose concentration.

All the above description and examples have been provided for the purpose of illustration and are not intended to limit the invention in any way.

The invention claimed is:

1. An isolated polypeptide comprising (a) the amino acid sequence set forth in SEQ ID NO: 21; or (b) an amino acid sequence that is at least 95% identical to SEQ ID NO: 21.

2. An isolated polypeptide according to claim 1, consisting of the amino acid sequence set forth in SEQ ID NO: 21.

3. An isolated polypeptide according to claim 1, wherein said polypeptide is modified at the N-terminal end with an acetyl moiety and at the C-terminal end with an amide moiety.

4. A pharmaceutical composition comprising an isolated polypeptide as defined in claim 1 and at least one pharmaceutically acceptable carrier, excipient, or diluent.

5. A method for lowering the blood glucose level in a subject, said method comprising administering a therapeutically effective amount of the polypeptide of claim 1 to said subject.

6. A method according to claim 5, wherein said subject suffers from a disease or disorder associated with hyperglycemia.

7. A method according to claim 6, wherein said disease or disorder is selected from the group consisting of diabetes mellitus type 1, diabetes mellitus type 2, nephropathy, retinopathy, cardiovascular diseases, glands dysfunction, pancreas diseases, sepsis, intracranial diseases, and post-surgery stress.

* * * * *